(12) United States Patent
Casellas et al.

(10) Patent No.: US 7,598,392 B2
(45) Date of Patent: Oct. 6, 2009

(54) 2-AMIDO-4-PHENYLTHIAZOLE DERIVATIVES, THE PREPARATION AND THE THERAPEUTIC USE THEREOF

(75) Inventors: Pierre Casellas, Montpellier (FR); Daniel Floutard, Combaillaux (FR); Pierre Fraisse, Juvignac (FR); Samir Jegham, Montferrier-sur-Lez (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 11/736,770

(22) Filed: Apr. 18, 2007

(65) Prior Publication Data

US 2007/0259847 A1 Nov. 8, 2007

Related U.S. Application Data

(63) Continuation of application No. PCT/FR2005/002565, filed on Oct. 17, 2005.

(30) Foreign Application Priority Data

Oct. 19, 2004 (FR) .................................. 04 11083

(51) Int. Cl.
*A61K 31/427* (2006.01)
*A61K 31/497* (2006.01)
*A61K 31/506* (2006.01)
*A61K 31/4545* (2006.01)
*C07D 417/14* (2006.01)

(52) U.S. Cl. .................. 548/195; 514/253.01; 514/269; 514/318; 514/370; 544/333; 544/364; 546/194; 546/209

(58) Field of Classification Search ................. 548/195
See application file for complete search history.

(56) References Cited

U.S. PATENT DOCUMENTS

| 4,225,610 | A | 9/1980 | Tarayre et al. |
| 5,314,889 | A | 5/1994 | Boigegrain et al. |
| 6,506,751 | B1 | 1/2003 | Justus et al. |
| 2002/0115863 | A1 | 8/2002 | Patel et al. |
| 2002/0119962 | A1 | 8/2002 | Jacobs et al. |
| 2004/0048891 | A1 | 3/2004 | Kato et al. |
| 2006/0135575 | A1 | 6/2006 | Carayon et al. |
| 2007/0179126 | A1 | 8/2007 | Casellas et al. |

FOREIGN PATENT DOCUMENTS

| EP | 0 001 727 | 5/1979 |
| EP | 0518731 | 12/1992 |
| EP | 0519449 | 12/1992 |
| EP | 1 344 525 A1 | 9/2003 |
| WO | WO 93/00342 | 1/1993 |
| WO | WO 02/051397 | 7/2002 |
| WO | WO 03/015778 | 2/2003 |
| WO | WO 03/088908 A2 | 10/2003 |
| WO | WO 2004/096796 | 11/2004 |
| WO | WO 2006/016039 A1 | 2/2006 |
| WO | WO 2006/067401 A1 | 6/2006 |
| WO | WO 2007/077394 | 7/2007 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
CA Registry No. 848256-98-4, indexed in the Registry file on STN on Apr. 11, 2005.*
CA Registry No. 848256-97-3, indexed in the Registry file on STN on Apr. 11, 2005.*
CA Registry No. 794538-35-5, indexed in the Registry file on STN on Dec. 8, 2004.*
CA Registry No. 749914-28-1, indexed in the Registry file on STN on Sep. 23, 2004.*
U.S. Appl. No. 12/146,898, filed Jun. 26, 2008, Fraisse et al.
Allen et al, Discovery And SAR Of Trisubstituted Thiazolidinones As CCR4 Antagonists, Bioorganic & Medicinal Chemistry Letters, Apr. 2004, 14:1619-1624.
Byrn et al, Hydrates and Solvates, Solid-State Chemistry of Drugs, Second Edition, 1999, pp. 233-247.
Lombardino et al., Potent Antiinflammatory N-Heterocyclic 3-Carboxamides of 4-Hyroxy-2-methyl-2H-1,2-benzothiazine 1,1-Dioxide, J. Med. Chem., 16 (5) pp. 493-496 (1973).
CA Registry No. 561003-70-1, entered STN on Aug. 5, 2003.
CA Registry No. 848298-35-1, entered STN on Apr. 12, 2005.
CA Registry No. 849040-28-4, entered STN on Apr. 22, 2005.

* cited by examiner

*Primary Examiner*—Laura L. Stockton
(74) *Attorney, Agent, or Firm*—Kelly L. Bender

(57) ABSTRACT

The disclosure relates to 2-amido-4-phenylthiazole derivatives of general formula (I) below:

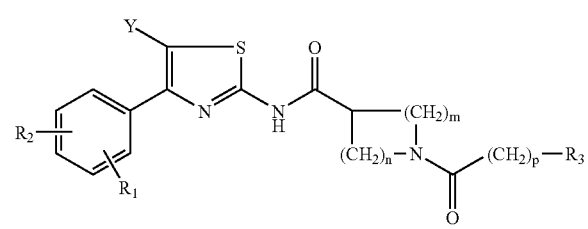

(I)

in which $R_1$, $R_2$, $R_3$, Y, m, n, and p are as defined in the disclosure; as well as to their isomers, salts and solvates, to the pharmaceutical compositions containing them and to the therapeutic use thereof.

17 Claims, No Drawings

2-AMIDO-4-PHENYLTHIAZOLE DERIVATIVES, THE PREPARATION AND THE THERAPEUTIC USE THEREOF

The invention relates to 2-amido-4-phenylthiazole derivatives, to their preparation and to their therapeutic application.

One subject of the invention is compounds corresponding to formula (I) below:

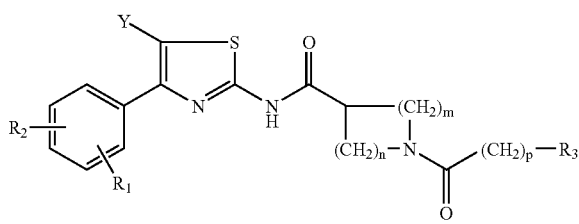

in which:

$R_1$ represents a hydrogen or halogen atom, a $(C_1-C_4)$alkyl, trifluoro$(C_1-C_4)$alkyl, hydroxyl, $(C_1-C_4)$alkoxy, trifluoro$(C_1-C_4)$alkoxy, $(C_3-C_{10})$cycloalkyl$(C_1-C_4)$alkoxy, $(C_3-C_{10})$cycloalkyloxy, allyloxy or $(C_1-C_4)$alkylthio group;

$R_2$ represents a hydrogen or halogen atom, a hydroxyl, $(C_1-C_4)$alkyl, trifluoro$(C_1-C_4)$alkyl, perfluoro$(C_1-C_4)$alkyl, $(C_3-C_{10})$cycloalkyl, $(C_1-C_4)$alkoxy, $(C_3-C_{10})$cycloalkyl$(C_1-C_4)$alkoxy, $(C_3-C_{10})$cycloalkyloxy, allyloxy or $(C_3-C_8)$cycloalkyl$(C_1-C_4)$alkyl group;

Y represents a hydrogen atom or a halogen;

$R_3$ represents:
- a phenyl group substituted with one or more halogen atoms and/or with one or more of the following groups:
  - $(C_1-C_6)$alkyl,
  - $(C_1-C_6)$alkoxy,
  - —$NO_2$,
  - cyano,
  - —$COR_4$,
  - —$SO_2R_4$,
  - —$CO_2R_4$, in which $R_4$ represents a $(C_1-C_4)$alkyl group,
  - —$(CH_2)_qNR_5R_6$, in which $R_5$ and $R_6$ represent, independently of each other, a hydrogen atom or a $(C_1-C_4)$alkyl group or $R_5$ and $R_6$ form, together with the nitrogen atom to which they are attached, a 5- or 6-membered cycloalkyl group and q represents 0, 1 or 2;
- a heterocyclic group optionally substituted with one or more halogens and/or with one or more of the following groups:
  - $(C_1-C_4)$alkyl,
  - hydroxyl,
  - $(C_1-C_4)$alkoxy,
  - cyano,
  - morpholine,
  - trifluoro$(C_1-C_4)$alkyl,
  - —$COR_4$,
  - —$SO_2R_4$, in which $R_4$ is as defined hereinabove,
  - —$(CH_2)_qNR_5R_6$ in which $R_5$, $R_6$ and q are as defined hereinabove,
  - phenyl,
  - pyridine,
  - —$SCH_3$;
- the nitrogen atom(s) of the heterocyclic group being optionally substituted with a $(C_1-C_4)$alkyl group, the nitrogen atom(s) of the heterocyclic group being optionally in their N-oxide form;
- a heterobicyclic group optionally substituted with one or more halogens and/or with one or more hydroxyl, $(C_1-C_4)$alkyl or $(C_1-C_4)$alkoxy groups;

m represents 2, 3 or 4;

n represents 0, 1 or 2;

p represents 0, 1, 2 or 3.

The compounds of the formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention.

These salts are advantageously prepared with pharmaceutically acceptable acids, but the salts of other acids that are useful, for example, for purifying or isolating the compounds of the formula (I) also form part of the invention.

The compounds of formula (I) may also exist in the form of hydrates or solvates, i.e. in the form of associations or combinations with one or more water molecules or with a solvent. Such hydrates and solvates also form part of the invention.

In the context of the present invention, the following definitions apply:

$(C_t-C_z)$ in which t and z may take values from 1 to 10, a carbon-based chain possibly containing from t to z carbon atoms, for example $(C_1-C_3)$ a carbon-based chain possibly containing from 1 to 3 carbon atoms;

Hal: a halogen atom such as a fluorine, a chlorine, a bromine or an iodine;

an alkyl group: a linear or branched saturated aliphatic group. Examples that may be mentioned include methyl, ethyl, propyl, isopropyl, butyl, isobutyl, tert-butyl, pentyl, etc. groups;

a cycloalkyl group: a cyclic alkyl group. Examples that may be mentioned include cyclopropyl, cyclobutyl, cyclopentyl, cyclohexyl, etc. groups;

an alkoxy group: an —O-alkyl group in which the alkyl group is as defined above;

a cycloalkyloxy group: an —O-cycloalkyl group in which the cycloalkyl group is as defined above;

an allyloxy group: —O-allyl;

a perfluoroalkyl group: an alkyl group as defined above, for which all the carbon atoms are substituted with fluorine atoms;

a heterocyclic group: an aromatic or non-aromatic cyclic group, comprising one or more hetero atoms such as nitrogen, oxygen, or sulfur. Examples of heterocyclic groups that may be mentioned include pyridyl, pyrazinyl, pyrimidinyl, pyridazinyl, pyrazolyl, imidazolyl, thiazolyl, isothiazolyl, oxazolyl, isoxazolyl, oxadiazolyl, thiophenyl, pyrrolyl and furyl groups;

a heterobicyclic group: a heterocyclic group as defined above, fused with another heterocyclic group or with a phenyl group. Examples of heterobicyclic groups that may be mentioned include the above heterocyclic groups fused with a phenyl nucleus, for example quinoxaline, quinoline, isoquinoline, indole, isoindole, indoline, indazole, benzothiazole, benzimidazole and benzoxazole groups;

a heterocyclic group in N-oxide form: a group having the following formula:

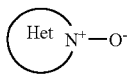

in which Het represents a heterocyclic group as defined hereinabove.

Among the compounds that are subjects of the invention, mention may be made of a first group of compounds of formula (I) in which:
$R_1$ and $R_2$ are as defined hereinabove;
Y represents a hydrogen atom or a halogen;
$R_3$ represents:
  a phenyl group substituted with one or more halogen atoms and/or with one or more of the following groups:
  $(C_1-C_6)$alkyl,
  $(C_1-C_6)$alkoxy,
  —$NO_2$,
  cyano,
  —$COR_4$,
  —$SO_2R_4$,
  —$CO_2R_4$, in which $R_4$ represents a $(C_1-C_4)$alkyl group,
  —$(CH_2)_qNR_5R_6$, in which $R_5$, $R_6$ and q are as defined hereinabove;
  a heterocyclic group optionally substituted with one or more halogens and/or with one or more of the following groups:
  $(C_1-C_4)$alkyl,
  hydroxyl,
  $(C_1-C_4)$alkoxy,
  cyano,
  morpholine,
  trifluoro$(C_1-C_4)$alkyl,
  —$COR_4$,
  —$SO_2R_4$, in which $R_4$ is as defined hereinabove,
  —$(CH_2)_qNR_5R_6$, in which $R_5$, $R_6$ and q are as defined hereinabove,
  phenyl,
  pyridine,
  —$SCH_3$;
  the nitrogen atom(s) of the heterocyclic group being optionally substituted with a $(C_1-C_4)$alkyl group,
  the nitrogen atom(s) of the heterocyclic group being optionally in their N-oxide form;
  a heterobicyclic group optionally substituted with one or more halogens and/or with one or more hydroxyl, $(C_1-C_4)$alkyl or $(C_1-C_4)$alkoxy groups;
m represents 3;
n represents 1;
p represents 0.

Among the compounds that are subjects of the invention, mention may be made of a second group of compounds of formula (I) in which:
$R_1$ and $R_2$ are as defined hereinabove;
Y is as defined hereinabove;
$R_3$ represents:
  a phenyl group substituted with one or more halogen atoms and/or with one or more of the following groups:
  $(C_1-C_6)$alkyl,
  $(C_1-C_6)$alkoxy,
  —$NO_2$,
  cyano,
  —$COR_4$,
  —$SO_2R_4$,
  —$CO_2R_4$, in which $R_4$ represents a $(C_1-C_4)$alkyl group,
  —$(CH_2)_qNR_5R_6$, in which $R_5$, $R_6$ and q are as defined hereinabove;
  a pyridyl, pyrazinyl, pyrimidinyl, pyridazinyl, pyrazolyl, imidazolyl, thiazolyl, isothiazolyl, oxazolyl, isoxazolyl, oxadiazolyl, thiophenyl, pyrrolyl or furyl group, the said groups being optionally substituted with one or more halogens and/or with one or more of the following groups:
  $(C_1-C_4)$alkyl,
  hydroxyl,
  $(C_1-C_4)$alkoxy,
  cyano,
  morpholine,
  trifluoro$(C_1-C_4)$alkyl,
  —$COR_4$,
  —$SO_2R_4$, in which $R_4$ is as defined hereinabove,
  —$(CH_2)_qNR_5R_6$, in which $R_5$, $R_6$ and q are as defined hereinabove,
  phenyl,
  pyridine,
  —$SCH_3$;
  the nitrogen atom(s) of the said groups mentioned above being optionally substituted with a $(C_1-C_4)$alkyl group,
  the nitrogen atom(s) of the said groups mentioned above being optionally in their N-oxide form;
  a quinoxaline, quinoline, isoquinoline, indole, isoindole, indoline, indazole, benzothiazole, benzimidazole or benzoxazole group, the said groups being optionally substituted with one or more halogens and/or with one or more hydroxyl, $(C_1-C_4)$alkyl or $(C_1-C_4)$alkoxy groups;
m represents 3;
n represents 1;
p represents 0.

Among the compounds that are subjects of the invention, mention may be made of a third group of compounds of formula (I) in which:
$R_1$ and $R_2$ are as defined hereinabove;
Y represents a hydrogen atom or a halogen;
$R_3$ represents:
  a phenyl group substituted with one or more halogen atoms and/or with one or more of the following groups:
  $(C_1-C_6)$alkyl,
  $(C_1-C_6)$alkoxy,
  —$NO_2$,
  cyano,
  —$COR_4$,
  —$SO_2R_4$,
  —$CO_2R_4$, $R_4$ representing a $(C_1-C_4)$alkyl group,
  —$(CH_2)_qNR_5R_6$, in which $R_5$, $R_6$ and q are as defined hereinabove;
  a heterocyclic group optionally substituted with one or more halogens and/or with one or more of the following groups:
  $(C_1-C_4)$alkyl,
  hydroxyl,
  $(C_1-C_4)$alkoxy,
  cyano,
  morpholine,
  trifluoro$(C_1-C_4)$alkyl,
  —$COR_4$,
  —$SO_2R_4$, in which $R_4$ is as defined hereinabove,
  —$(CH_2)_qNR_5R_6$, in which $R_5$, $R_6$ and q are as defined hereinabove, phenyl,
pyridine,
—SCH$_3$;
  the nitrogen atom(s) of the heterocyclic group being optionally substituted with a (C$_1$-C$_4$)alkyl group,
  the nitrogen atom(s) of the heterocyclic group being optionally in their N-oxide form;
  a heterobicyclic group optionally substituted with one or more halogens and/or with one or more hydroxyl, (C$_1$-C$_4$)alkyl or (C$_1$-C$_4$)alkoxy groups;
m represents 2 or 4; and/or
n represents 0, 1 or 2; and/or
p represents 0, 1 or 2.

Among the compounds that are subjects of the invention, mention may be made of a fourth group of compounds of formula (I) in which:
R$_1$ and R$_2$ are as defined hereinabove;
Y represents a hydrogen atom or a halogen;
R$_3$ represents:
  a phenyl group substituted with one or more halogen atoms and/or with one or more of the following groups:
    (C$_1$-C$_6$)alkyl,
    (C$_1$-C$_6$)alkoxy,
    —NO$_2$,
    cyano,
    —COR$_4$,
    —SO$_2$R$_4$,
    —CO$_2$R$_4$, in which R$_4$ represents a (C$_1$-C$_4$)alkyl group,
    —(CH$_2$)$_q$NR$_5$R$_6$, in which R$_5$, R$_6$ and q are as defined hereinabove;
  a pyridyl, pyrazinyl, pyrimidinyl, pyridazinyl, pyrazolyl, imidazolyl, thiazolyl, isothiazolyl, oxazolyl, isoxazolyl, oxadiazolyl, thiophenyl, pyrrolyl or furyl group, the said groups being optionally substituted with one or more halogens and/or with one or more of the following groups:
    (C$_1$-C$_4$)alkyl,
    hydroxyl,
    (C$_1$-C$_4$)alkoxy,
    cyano,
    morpholine,
    trifluoro(C$_1$-C$_4$)alkyl,
    —COR$_4$,
    —SO$_2$R$_4$, in which R$_4$ is as defined hereinabove,
    —(CH$_2$)$_q$NR$_5$R$_6$, in which R$_5$, R$_6$ and q are as defined hereinabove,
    phenyl,
    pyridine,
    —SCH$_3$;
    the nitrogen atom(s) of the said groups mentioned above being optionally substituted with a (C$_1$-C$_4$)alkyl group,
    the nitrogen atom(s) of the said groups mentioned above being optionally in their N-oxide form;
  a quinoxaline, quinoline, isoquinoline, indole, isoindole, indoline, indazole, benzothiazole, benzimidazole or benzoxazole group, the said abovementioned groups being optionally substituted with one or more halogens and/or with one or more hydroxyl, (C$_1$-C$_4$)alkyl or (C$_1$-C$_4$)alkoxy groups;
m represents 2 or 4; and/or
n represents 0, 1 or 2; and/or
p represents 0, 1 or 2.

Among the compounds that are subjects of the invention, mention may be made of a fifth group of compounds of formula (I) in which:
R$_1$ and R$_2$ are as defined hereinabove;
Y represents a hydrogen atom or a halogen;
R$_3$ represents:
  a phenyl group substituted with one or more halogen atoms and/or with one or more of the following groups:
    (C$_1$-C$_6$)alkyl,
    (C$_1$-C$_6$)alkoxy,
    —NO$_2$,
    cyano,
    —COR$_4$,
    —SO$_2$R$_4$,
    —CO$_2$R$_4$, in which R$_4$ represents a (C$_1$-C$_4$)alkyl group,
    —(CH$_2$)$_q$NR$_5$R$_6$, in which R$_5$, R$_6$ and q are as defined hereinabove;
  a pyridyl, pyrazinyl, pyrimidinyl, pyridazinyl, pyrazolyl, imidazolyl, thiazolyl, isothiazolyl, oxazolyl, isoxazolyl, oxadiazolyl, thiophenyl, pyrrolyl or furyl group, the said abovementioned groups being optionally substituted with one or more halogens and/or with one or more of the following groups:
    (C$_1$-C$_4$)alkyl,
    hydroxyl,
    (C$_1$-C$_4$)alkoxy,
    cyano,
    morpholine,
    trifluoro(C$_1$-C$_4$)alkyl,
    —COR$_4$,
    —SO$_2$R$_4$, in which R$_4$ is as defined hereinabove,
    —(CH$_2$)$_q$NR$_5$R$_6$, in which R$_5$, R$_6$ and q are as defined hereinabove,
    phenyl,
    pyridine,
    —SCH$_3$;
    the nitrogen atom(s) of the said groups mentioned above being optionally substituted with a (C$_1$-C$_4$)alkyl group,
    the nitrogen atom(s) of the said groups mentioned above being optionally in their N-oxide form;
  a quinoxaline, quinoline, isoquinoline, indole, isoindole, indoline, indazole, benzothiazole, benzimidazole or benzoxazole group, the said abovementioned groups being optionally substituted with one or more halogens and/or with one or more hydroxyl, (C$_1$-C$_4$)alkyl or (C$_1$-C$_4$)alkoxy groups;
m represents 2 or 4; and/or
n represents 0, 1 or 2; and/or
p represents 0.

Compounds of formula (I) according to the invention are those in which R$_1$ is in position 2 of the phenyl and R$_2$ is in position 5 of the phenyl.

Compounds of formula (I) according to the invention are those in which R$_1$ is in position 2 of the phenyl, R$_1$ especially representing a (C$_1$-C$_4$)alkoxy group, and R$_2$ is in position 5 of the phenyl, R$_2$ especially representing a (C$_1$-C$_4$)alkoxy, (C$_1$-C$_4$)alkyl or (C$_3$-C$_{10}$) cycloalkyl group.

Among the compounds of formula (I) of the invention that may especially be mentioned are the following compounds:
1-(1,5-dimethyl-1H-pyrazole-3-carbonyl)piperidine-3-carboxylic acid [4-(5-cyclohexyl-2-methoxyphenyl)thiazol-2-yl]amide (compound 114),
1-(1-methyl-1H-imidazole-2-carbonyl)piperidine-3-carboxylic acid [4-(5-cyclohexyl-2-methoxyphenyl)thiazol-2-yl]amide (compound 112),
1-(pyrimidine-4-carbonyl)piperidine-3-carboxylic acid [4-(5-cyclohexyl-2-methoxyphenyl)thiazol-2-yl]amide (compound 107),
1-(pyrazine-2-carbonyl)piperidine-3-carboxylic acid [4-(5-cyclohexyl-2-ethoxyphenyl)thiazol-2-yl]amide (compound 98), 1-(1-oxypyridine-2-carbonyl)piperidine-3-carboxylic acid [4-(5-cyclopentyl-2-methoxyphenyl)thiazol-2-yl]amide (compound 118),
1-(2-hydroxypyridine-3-carbonyl)piperidine-3-carboxylic acid [4-(5-cyclohexyl-2-methoxyphenyl)thiazol-2-yl]amide (compound 101),
1-(1-oxypyridine-3-carbonyl)piperidine-3-carboxylic acid [4-(5-cyclohexyl-2-methoxyphenyl)thiazol-2-yl]amide (compound 115),
1-(5-chloro-1-methyl-1H-pyrazole-4-carbonyl)piperidine-3-carboxylic acid [4-(5-cyclohexyl-2-methoxyphenyl)thiazol-2-yl]amide (compound 27),
1-(furan-2-carbonyl)piperidine-3-carboxylic acid [4-(5-cyclohexyl-2-methoxyphenyl)thiazol-2-yl]amide (compound 28),
1-(pyrazine-2-carbonyl)piperidine-4-carboxylic acid [4-(5-cyclohexyl-2-methoxyphenyl)thiazol-2-yl]amide (compound 120),
1-(pyrazine-2-carbonyl)piperidine-2-carboxylic acid [4-(5-cyclohexyl-2-methoxyphenyl)thiazol-2-yl]amide (compound 109),
1-(2-pyridin-2-ylacetyl)piperidine-3-carboxylic acid [4-(5-cyclohexyl-2-methoxyphenyl)thiazol-2-yl]amide (compound 60),
1-(1-oxypyridine-2-carbonyl)piperidine-3-carboxylic acid [4-(5-cyclohexyl-2-methoxyphenyl)thiazol-2-yl]amide (compound 102),
(S)-1-(1-oxypyridine-2-carbonyl)piperidine-3-carboxylic acid [4-(5-cyclohexyl-2-methoxyphenyl)thiazol-2-yl]amide (compound 124),
1-(pyrazine-2-carbonyl)piperidine-3-carboxylic acid [4-(5-cyclohexyl-2-methoxyphenyl)thiazol-2-yl]amide (compound 97),
(S)-1-(pyrazine-2-carbonyl)piperidine-3-carboxylic acid [4-(5-cyclohexyl-2-methoxyphenyl)thiazol-2-yl]amide (compound 108),
1-(1-oxypyridine-2-carbonyl)piperidine-3-carboxylic acid [4-(5-butyl-2-methoxyphenyl)thiazol-2-yl]amide (compound 117),
1-(pyrazine-2-carbonyl)piperidine-3-carboxylic acid [4-(5-cyclopentyl-2-methoxyphenyl)thiazol-2-yl]amide (compound 100),
(R)-1-(pyrazine-2-carbonyl)piperidine-3-carboxylic acid [4-(5-cyclohexyl-2-methoxyphenyl)thiazol-2-yl]amide (compound 121),
1-(1-oxypyridine-2-carbonyl)pyrrolidine-3-carboxylic acid [4-(5-cyclohexyl-2-methoxyphenyl)thiazol-2-yl]amide (compound 105),
(R)-1-(1-oxypyridine-2-carbonyl)pyrrolidine-3-carboxylic acid [4-(5-cyclohexyl-2-methoxyphenyl)thiazol-2-yl]amide (compound 239).

A subject of the invention is also a process for preparing the compounds of formula (I).

In the text hereinbelow, the term "protecting group Pg" means a group that makes it possible firstly to protect a reactive function such as a hydroxyl or an amine during a synthesis, and secondly to regenerate the intact reactive function at the end of the synthesis. Examples of protecting groups and of protection and deprotection methods are given in "Protective Groups in Organic Synthesis", Greene et al., $2^{nd}$ Edition (John Wiley & Sons, Inc., New York).

In the text hereinbelow, the term "leaving group X" means a group that can be readily cleaved from a molecule by breaking a heterolytic bond, with loss of an electron pair. This group may thus be readily replaced with another group during a substitution reaction, for example. Such leaving groups are, for example, halogens or an activated hydroxyl group such as a mesyl, tolsyl, triflate, acetyl, etc. Examples of leaving groups and of references for preparing them are given in "Advances in Organic Chemistry", J. March, $3^{rd}$ Edition, Wiley Interscience, pp. 310-316.

In the text hereinbelow, the term "precursor of $R_1$ and/or $R_2$" means a substituent $R'_1$ and/or $R'_2$ that may be converted into $R_1$ and/or $R_2$ via one or more chemical reactions known to those skilled in the art, or $R_1$ and/or $R_2$ represent $R_1$ and/or $R_2$.

In the text hereinbelow, the term "group Z" means a leaving group or a functional derivative derived from an acid function, such as an acid chloride, a mixed or symmetrical anhydride, or alternatively the acid appropriately activated, for example with benzotriazol-1-yloxytris(dimethylamino) phosphonium hexafluorophosphate (BOP), O-benzotriazol-1-yl-N,N,N',N'-tetramethyluronium hexafluorophosphate (HBTU) or O-benzotriazol-1-yl-N,N,N',N'-tetramethyluronium tetrafluoroborate (TBTU).

When one or more substituents $R'_1$ and/or $R'_2$ represent a group containing an amine or hydroxyl function, these functions may be intermediately protected: an amine function may be protected with an alkanoyl, benzyl, tert-butoxycarbonyl (Boc), benzyloxycarbonyl or 9-fluorenylmethoxycarbonyl (Fmoc) group, for example; a hydroxyl function may be protected in ether or ester form, for example.

The compounds of the invention may be prepared according to various methods described hereinbelow.

Before addressing these methods, the methods for preparing the aminothiazole derivatives of formula (II) that are used for the preparation of the compounds of formula (I) of the invention are described below.

In the text hereinbelow:

THF=tetrahydrofuran,

BOP=benzotriazol-1-yloxytris(dimethylamino)-phosphonium hexafluorophosphate,

CDI=1,1'-carbonyldiimidazole,

DMF=dimethylformamide,

TMS=tetramethylsilane,

DMSO=dimethyl sulfoxide,

DCM=dichloromethane,

TBTU=2-(1H-benzotriazol-1-yl)-1,1,3,3-tetramethyluronium tetrafluoroborate.

The aminothiazole derivatives of formula (II) may be prepared via known methods such as those described in documents EP 518 731, EP 611 766 and WO 99/15525.

In general, when Y=H, thiourea is reacted with a halo ketone of formula 1 according to the following reaction scheme:

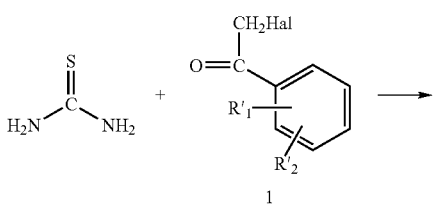

-continued

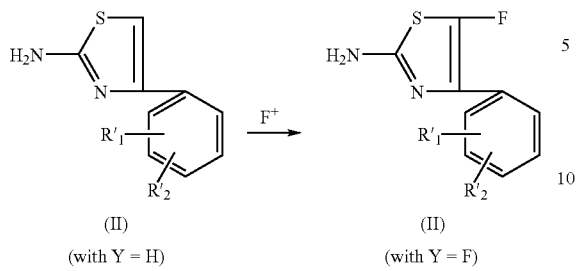

(II)
(with Y = H)

(II)
(with Y = F)

The substituents $R'_1$ and $R'_2$ have the values indicated above, i.e. $R'_1$ and $R'_2$ represent, respectively, $R_1$ and $R_2$ as defined for the compound of general formula (I) or precursor groups of $R_1$ and $R_2$; Hal represents a halogen atom, preferably bromine, chlorine or iodine.

As indicated in the above scheme, the compounds of the type (II) with Y=H, $R'_1$ and $R'_2$ having the values indicated above, may be converted into compounds of the type (II) with Y=F and $R'_1$ and $R'_2$ having the values indicated above by reaction with a fluorinating agent, for instance Selectfluor™ in a solvent such as DMF or DCM, at a temperature ranging from 0° C. to 50° C.

The halo ketones of formula 1 may be prepared via processes known to those skilled in the art. For example, the bromo ketones may be obtained via the action of bromine, cupric bromide or phenyltrimethylammonium tribromide (PTT) on an acetophenone derivative of formula 2:

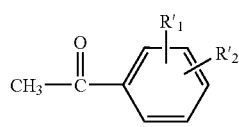

2 in which $R'_1$ and $R'_2$ have the values indicated above, in an organic solvent such as ethyl acetate, a chlorinated solvent or a mixture thereof, or alternatively an alcohol.

When the acetophenone derivative of formula 2 is not commercially available, it may be prepared via various methods:

a Friedel-Crafts reaction on benzene substituted with $R'_1$ and $R'_2$ that is reacted with acetyl chloride or acetic anhydride, in the presence of a Lewis acid such as $AlCl_3$ or $TiCl_4$, for example;

the action of acetyl chloride in the presence of palladium on benzene substituted with $R'_1$ and $R'_2$ after deprotonation of the benzene, for example via the action of butyllithium, followed by addition of zinc chloride or manganese iodide. This procedure may be used to prepare an acetophenone derivative of formula 2 in which $R'_2=R_2=(C_1-C_4)$perfluoroalkyl;

a Fries rearrangement starting with an acetoxybenzene derivative of formula 3:

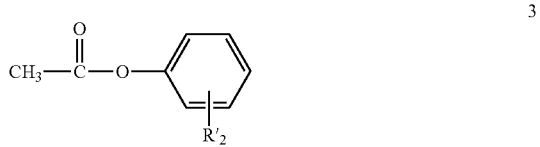

3 via the action of a Lewis acid, to give a hydroxyacetophenone derivative of formula 4:

4

The hydroxyl function corresponds to a group $R'_1$ that can be converted in a subsequent step into a group —O—W such as $(C_1-C_8)$alkoxy, trifluoromethoxy, trifluoroethoxy, allyloxy, $(C_3-C_{10})$cycloalkylmethoxy or $(C_3-C_{10})$ cycloalkyloxy.

The conversion of $R'_1$ into $R_1$ may be performed either on the aminothiazole of formula (II) or on a compound of formula (I).

The benzene derivatives substituted with $R'_1$ and $R'_2$ are commercially available or are prepared via methods known to those skilled in the art.

For example, to prepare a compound in which $R_1$ is a group —O—W as defined above, the process is performed in the following manner:

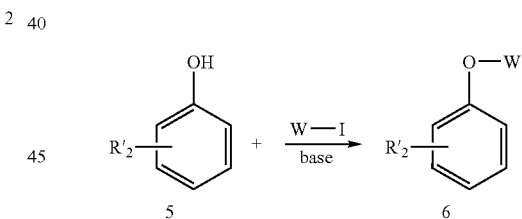

5      6

A halobenzene derivative may also be substituted according to the following scheme:

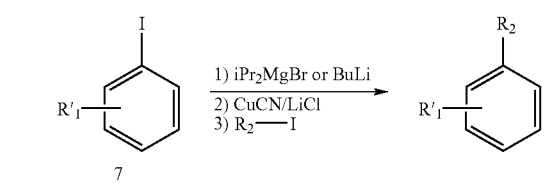

7

In the particular case in which $R_2$ represents a $(C_1-C_4)$ perfluoroalkyl, the process may also be performed according to the following reaction scheme:

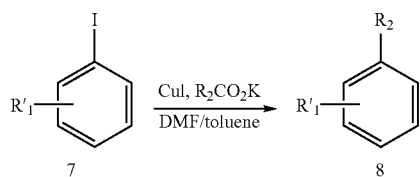

Examples of preparation of aminothiazole derivatives of formula (II) are given as illustrations hereinbelow.

The compounds of formula (I) of the invention may be prepared according to the general Scheme 1 below.

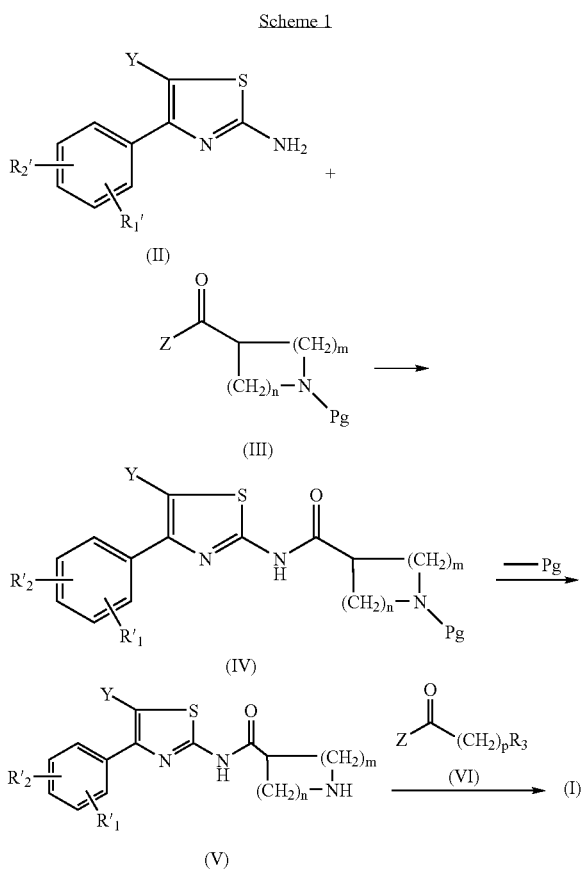

According to Scheme 1, a compound of formula (II) in which Y, $R'_1$ and $R'_2$ are as defined hereinabove is coupled with a compound of formula (III) in which Z, Pg, m and n are as defined hereinabove, via an acylation or a coupling of peptide type, in the presence of a base such as $K_2CO_3$, triethylamine, caesium carbonate or a coupling reagent, for instance BOP, TBTU or CDI, in a solvent chosen from THF, acetonitrile and DMF especially, at temperatures of between 0° C. and 150° C. The compound of formula (IV) thus obtained is deprotected to give the amine derivative of formula (V). In the compound of formula (IV), Y, m, n, Pg, $R'_1$ and $R'_2$ are as defined hereinabove. The compound of formula (V) in which Y, m, n, $R'_1$ and $R'_2$ are as defined hereinabove is then reacted with an acid or an acid derivative of formula (VI) in which $R_3$, Z and p are as defined hereinabove, in the presence of a base such as $K_2CO_3$, triethylamine or caesium carbonate or a coupling reagent, for instance BOP, TBTU or CDI, in a solvent chosen from THF, acetonitrile and DMF especially, at temperatures of between 0° C. and 150° C.

When the compounds of formula (III) are not commercially available, they may be prepared using the processes described in the literature, for example in the publication H. Rapoport, J. Org. Chem. 1974, 39, 893 and in document WO 97/41102.

The compounds of type (I) may also be prepared according to Scheme 2 below:

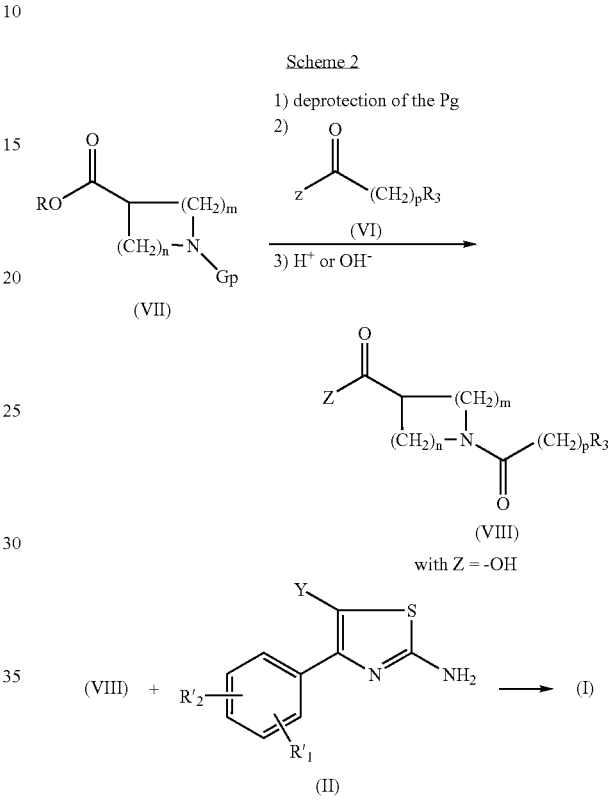

According to Scheme 2, a compound of formula (VII) in which R represents a $(C_1-C_4)$alkyl group and Pg represents a protecting group as defined hereinabove is deprotected and then condensed with a compound of formula (VI) in which $R_3$, Z and p are as defined hereinabove, in the presence of a base such as $K_2CO_3$, triethylamine or caesium carbonate or a coupling reagent, for instance BOP, TBTU or CDI, in a solvent chosen from THF, acetonitrile and DMF especially, at temperatures of between 0° C. and 150° C. An acid derivative of formula (VIII) is obtained after saponification or acid hydrolysis. The compound of formula (VIII) in which $R_3$, m, n and p are as defined hereinabove is then condensed with a compound of formula (II) as defined above, in the presence of a base such as $K_2CO_3$, triethylamine or caesium carbonate or a coupling reagent, for instance BOP, TBTU or CDI, in a solvent chosen from THF, acetonitrile and DMF especially, at temperatures of between 0° C. and 150° C., to obtain the compounds of formula (I).

The compounds of formula (VII) and the deprotected derivatives thereof are commercially available or may be prepared using the processes described in document WO 92/15585.

In the two general Schemes 1 and 2 described above, compound (VI) is commercially available or may be obtained by homologation of the commercial carboxylic acid according to standard methods, such as reactions of Arndt-Eistert type (Tet. Lett., 1979, 29, 2667 "Advanced in Organic Chemistry", J. March, 3$^{rd}$ Edition, Wiley Interscience, pp. 1405-1407), according to the following scheme:

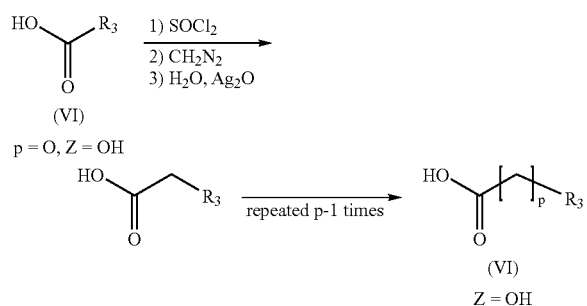

p = O, Z = OH

In the examples that follow, when compound (VI) with p=0 and Z=—OH is not commercially available, it is prepared according to the process described in J. Med. Chem. 1977, 20, 1312.

In the general synthetic Schemes 1 and 2, the starting compounds and the reagents, when their mode of preparation is not described, are commercially available or described in the literature, or alternatively may be prepared according to methods described therein or known to those skilled in the art.

According to another of its aspects, a subject of the invention is also the compounds of formula (V') below:

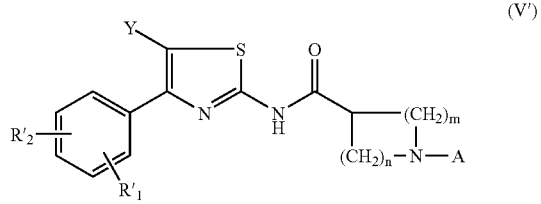

in which R'$_1$ and R'$_2$ represent precursors of R$_1$ and R$_2$ as defined hereinabove, Y, m and n are as defined hereinabove and A represents a hydrogen atom or a group Pg as defined for the compounds of formulae (IV) and (V).

These compounds are useful as intermediates for the synthesis of the compounds of formula (I). Examples of compounds of formula (V') are given in Table II below.

The examples that follow describe the preparation of compounds of formula (I) in accordance with the invention. These examples are not limiting and serve merely to illustrate the invention. The numbers of the illustrated compounds refer to those given in Table III, which illustrates the chemical structures and the physical properties of a number of compounds according to the invention.

The numbers of the preparations of the compounds of formula (II) refer to those given in Table I.

In the preparations and examples that follow:
RT=room temperature,
DCM=dichloromethane,
DIPEA=diisopropylethylamine,
THF=tetrahydrofuran,
BOP=benzotriazol-1-yloxytris(dimethylamino)-phosphonium hexafluorophosphate,
DMF=dimethylformamide,
Boc=tert-butyloxycarbonyl,
TFA=trifluoroacetic acid,
TBTU=2-(1H-benzotriazol-1-yl)-1,1,3,3-tetramethyluronium tetrafluoroborate,
HOBT=hydroxybenzotriazole,
BSA=bis(trimethylsilyl)acetamide,
EtOAc=ethyl acetate,
AcCl=acetyl chloride,
m.p.=melting point (in degrees Celsius) as measured on a Büchi B545 machine with a temperature gradient of 1° C. per minute,
MH+=mass spectrum. The compounds are analysed by HPLC-UV-MS coupling (liquid chromatography-UV detection-mass spectrometry). The machine used, sold by Agilent, is composed of an HP1100 chromatograph equipped with an Agilent diode array detector and an MSD Quad quadripolar mass spectrometer.

The analytical conditions are as follows:
Column: symmetry C18 (50×2.1 mm; 3.5 µm)
Eluent A: H$_2$O+0.005% TFA at pH 3.15
Eluent B: CH$_3$CN+0.005% TFA
Gradient:

| Time (min) | % B |
|---|---|
| 0 | 0 |
| 10 | 90 |
| 15 | 90 |
| 16 | 0 |
| 20 | 0 |

Column temperature: 30° C.
Flow rate: 0.4 mL/min
Detection: λ=210 nm
rt—retention time,
NMR=nuclear magnetic resonance performed with a Bruker Avance 200 spectrometer (200 MHz). The solvent used is deuterated DMSO and the chemical shifts are expressed relative to TMS. The abbreviations used are:
s=singlet,
d=doublet,
dd=doubled doublet,
t=triplet,
m=multiplet,
bs=broad singlet, §
the optical purity is measured by HPLC on a Chiralpak AD column (250 mm×4.6) eluted with an 80/20 CO$_2$/MeOH mixture at 30° C. with a flow rate of 3 mL/min at P=20 MPa. The compounds are detected at 220 nm,
α$_D$=optical rotation. The optical rotations are determined with a Perkin-Elmer 241-MC polarimeter for the sodium D line (λ=589 nm), the concentrations are expressed in 10 mg/mL, and the measurements are taken at room temperature.

I. Preparation of Aminothiazole Derivatives of Formula (II)

Preparation I.1

4-(2-Methoxy-5-propoxyphenyl)-1,3-thiazol-2-amine

A) 1-(2-Hydroxy-5-propoxyphenyl)ethanone 10 g of 2,5-dihydroxyacetophenone suspended in 100 mL of acetone are placed in a 500 mL round-bottomed flask and 9.14 g of anhydrous K$_2$CO$_3$ are added, followed by addition of 12.4 g of propyl iodide. The reaction medium is refluxed for 30 hours. After cooling to room temperature, the medium is filtered through Celite® and then concentrated. The brown oil obtained is taken up in EtOAc, filtered, washed with water, with 2 M HCl solution and then with saturated NaCl solution. The organic phase is evaporated to give a black paste. The paste is taken up in chloroform and filtered. The medium is concentrated to give 11.4 g of a black solid. This solid is taken up in absolute ethanol. The solution is placed in a freezer for 10 minutes, and a solid precipitates and is collected by filtration. The filtrate is concentrated, taken up in ethanol, cooled in the freezer and then filtered again. This operation is repeated 4 times to give 8.35 g of the expected compound in the form of a powder.

B) 1-(2-Methoxy-5-propoxyphenyl)ethanone

To a solution of 35 g of the above solid in 350 mL of DMF are added 49.8 g of $K_2CO_3$, followed by addition of 22.4 mL of methyl iodide. The reaction medium is heated for 12 hours at 60° C. After cooling to room temperature, the medium is filtered through Celite®, diluted in ether and washed with 2 M HCl solution. The aqueous phase is extracted twice with ether. The combined organic phases are washed with dilute sodium hydroxide solution and then washed twice with water and with saturated NaCl solution. The organic phase is dried over $MgSO_4$ and then evaporated to give 35.55 g of a brown oil. The oil is distilled under reduced pressure at 115° C. to give 32.8 g of the expected compound in the form of an oil.

C)
2-Bromo-1-(2-methoxy-5-propoxyphenyl)ethanone

To a solution of 16.4 g of the oil obtained in the preceding step in 100 mL of methanol are added dropwise 4.8 mL of bromine. The medium is stirred for 30 minutes at room temperature and then evaporated. The oil obtained is taken up in dichloromethane, washed 3 times with water and then dried over $MgSO_4$ and evaporated to give 24.5 g of a brown oil.

D) 4-(2-Methoxy-5-propoxyphenyl)-1,3-thiazol-2-amine

To a solution of 42 g of the bromo ketone prepared in the above step in 200 mL of ethanol are added 24.5 g of thiourea. The medium is refluxed for 1 hour 30 minutes. The medium is then placed in a refrigerator for 12 hours, and then filtered. The solid thus collected is rinsed with a small amount of cold ethanol and then with ether. 25 g of hydrobromide are recovered.

The solid is suspended in a water/dichloromethane mixture and basified by addition of sodium hydroxide. The aqueous phase is extracted twice with dichloromethane. The combined organic phases are dried over $MgSO_4$ and then evaporated. The oil obtained is chromatographed on silica gel to give 12 g of the expected product in the form of a powder.
m.p.=76° C.

Preparation I.2

4-(5-Butyl-2-methoxyphenyl)-1,3-thiazol-2-amine

A) 4-Butylphenyl acetate

A solution of 10 g of 4-n-butylphenol, 10 mL of $Ac_2O$ and 8 mL of pyridine is stirred at reflux in 10 mL of dichloromethane. After 2 hours, the medium is cooled to room temperature, diluted with dichloromethane, washed with water, washed with 1 M HCl solution, washed with saturated $CuSO_4$ solution, washed with water and dried over $MgSO_4$. After evaporation, 10.8 g of the expected compound are recovered in the form of an oil.

B) 1-(5-Butyl-2-hydroxyphenyl)ethanone

To 5 g of the oil obtained in the above step in a 100 mL round-bottomed flask are added 3.22 g of $AlCl_3$ in several portions. The medium is heated at 130° C. for 1 hour. After cooling to room temperature, a solution of ice-cold water acidified with 35% HCl is added to the crude reaction product. The medium is placed in an ultrasonic bath. EtOAc is added to obtain, after 15 minutes, dissolution of the medium. The aqueous phase is extracted 3 times with EtOAc and the organic phases are washed with water and then with saturated NaCl solution. After drying over $MgSO_4$ and evaporation, 4.5 g of a yellow oil are recovered.

C) 1-(5-Butyl-2-methoxyphenyl)ethanone

To a solution of 1 g of the oil obtained in the above step in 10 mL of DMF are added 1.44 g of $K_2CO_3$, followed by addition of 0.648 mL of methyl iodide. The medium is heated at 60° C. overnight. After cooling to room temperature, the medium is filtered through Celite®, diluted with ether and washed with 2 M HCl solution. The aqueous phase is extracted twice with ether. The combined organic phases are washed with dilute sodium hydroxide solution and then washed twice with water and with saturated NaCl solution. The organic phase is dried over $MgSO_4$ and then evaporated to give 1.27 g of a brown oil. The oil is purified by chromatography to give 0.66 g of the expected compound.

D) 4-(5-Butyl-2-methoxyphenyl)-1,3-thiazol-2-amine

To a solution of 0.66 g of the product from the above step in 10 mL of methanol is added 0.19 mL of bromine. The medium is stirred for 10 minutes and then evaporated and taken up in dichloromethane. The organic phase is washed 3 times with water and then dried over $MgSO_4$. 0.79 g of the expected product is recovered after evaporation. This compound is dissolved in 5 mL of ethanol in the presence of 0.46 g of thiourea and the medium is refluxed for 2 hours 30 minutes. A solid precipitates out on cooling to room temperature. The solid thus collected is rinsed with a small amount of cold ethanol and then with ether. 0.6 g of the hydrobromide is thus recovered.

The solid is suspended in a water/dichloromethane mixture and basified by addition of sodium hydroxide. The aqueous phase is extracted twice with dichloromethane. The combined organic phases are dried over $MgSO_4$ and then evaporated to give 0.34 g of a yellow oil that crystallizes slowly. The mother liquors are evaporated and then stirred in a water/dichloromethane mixture and basified by addition of sodium hydroxide. The aqueous phase is extracted twice with dichloromethane. The combined organic phases are dried over $MgSO_4$ and then evaporated. The oil obtained is chromatographed on silica gel to give 0.18 g of the expected compound.
m.p.=48° C.

Preparation I.22

4-(5-Pentafluoroethyl-2-methoxyphenyl)-1,3-thiazol-2-amine

A) 1-Methoxy-4-pentafluoroethylbenzene 8.3 g of potassium pentafluoropropionate and 9.8 g of CuI are introduced, under an inert atmosphere, into a 500 mL three-necked flasked equipped with Dean-Stark apparatus and a condenser. 90 mL of DMF and 110 mL of toluene are added. The medium is heated to 140° C. under nitrogen, and 80 mL of toluene are distilled off. The medium is then cooled to RT and then deoxygenated by sparging with nitrogen. 6 g of iodoanisole are then added and the mixture is then heated at 155° C. for 20 hours. After cooling to RT, the medium is diluted with 200 mL of a water/ethyl ether mixture. The medium is then filtered through Celite®. The organic phase is washed 3 times with water, dried over MgSO$_4$ and then evaporated to give 4.3 g of a brown oil.

B) 1-(2-Methoxy-5-pentafluoroethylphenyl)ethanone

To a solution of 3.5 g of 1-methoxy-4-pentafluoroethyl-benzene in 50 mL of anhydrous THF are added, at −70° C., 7.4 mL of 2.5 M BuLi in hexane. The medium is stirred for 30 minutes at −70° C. and then for 45 minutes at 0° C. 15.5 mL of a 1 M solution of zinc chloride in ether are then added. After stirring for 10 minutes at 0° C., 1.33 mL of acetyl chloride are added. The medium is then deoxygenated with nitrogen and 332 mg of benzyl(chloro)bis(triphenylphosphine)-palladium in 5 mL of anhydrous THF are introduced. The medium is stirred for 2 hours 30 minutes at 0° C. and then for 72 hours at RT. The medium is poured onto a 2.5 M HCl solution and then extracted with ether. The organic phase is washed with 5% NaHCO$_3$ in water, with water and then with saturated NaCl solution. After drying over MgSO$_4$ and evaporation, the crude product is purified by flash chromatography on silica to give 2.25 g of a white solid.

m.p.=47° C.

C) 4-(5-Pentafluoroethyl-2-methoxyphenyl)-1,3-thiazol-2-amine

To a solution of 2.25 g of the product obtained in the preceding step in 10 mL of methanol is added 0.5 mL of bromine dissolved in 8 mL of methanol. The medium is stirred for 10 minutes and then evaporated and taken up in dichloromethane. The organic phase is washed 3 times with water and then dried over MgSO$_4$. 2.63 g of the bromo product are recovered after evaporation. This compound is dissolved in 15 mL of methanol in the presence of 1.25 g of thiourea and the medium is refluxed for 2 hours. A solid precipitates out on cooling to RT. The solid thus collected is rinsed with ethyl ether. The solid is suspended in a water/dichloromethane mixture and basified by addition of sodium hydroxide. The aqueous phase is extracted twice with dichloromethane. The combined organic phases are dried over MgSO$_4$ and then evaporated to give 1.63 g of a yellow solid.

m.p.=125° C.

Preparation I.3

4-(5-Cyclohexyl-2-methoxyphenyl)-1,3-thiazol-2-amine

A) To a solution of 5 g of 4-cyclohexylphenol in 60 mL of DMF are added 7.84 g of K$_2$CO$_3$, followed by addition of 3.53 mL of methyl iodide. The medium is heated at 60° C. overnight. After cooling to room temperature, the medium is filtered through Celite® and then diluted with ether and hydrolysed with water. The aqueous phase is acidified and then extracted with 3 times 50 mL of ether. The combined organic phases are washed with dilute sodium hydroxide solution, and then washed twice with water and with saturated NaCl solution. The organic phase is dried over MgSO$_4$ and then evaporated to give 4.31 g of the expected compound in the form of a solid.

m.p.=67° C.

B) 1-(5-Cyclohexyl-2-methoxyphenyl)ethanone

A suspension of 5.6 g of AlCl$_3$ in 40 mL of dichloromethane is cooled to −10° C. 3 mL of AcCl and 4 g of the compound obtained in the preceding step are added. The medium is stirred for 1 hour at −10° C. and then poured into a beaker containing ice mixed with 35% HCl. After separation of the phases by settling, the combined organic phases are dried over MgSO$_4$ and then evaporated to give 4.54 g of the expected product.

C) 4-(5-Cyclohexyl-2-methoxyphenyl)-1,3-thiazol-2-amine

To a solution of 4.5 g of the product from the preceding step in 25 mL of methanol are added dropwise 1.16 mL of bromine. The medium is stirred for 30 minutes at room temperature and then becomes very viscous. 5 mL of methanol are added, followed by addition of 3.23 g of thiourea. The medium is refluxed for 2 hours. After cooling to room temperature, a solid precipitates out. The solid is collected and then rinsed with a small amount of cold methanol. The solid is suspended in a water/dichloromethane mixture and basified by addition of sodium hydroxide. The aqueous phase is extracted twice with dichloromethane. The combined organic phases are dried over MgSO$_4$ and then evaporated to give 3.33 g of the expected compound in the form of a solid.

m.p.=113° C.

Preparation I.4

4-(2-Methoxy-5-propylphenyl)-1,3-thiazol-2-amine

A) 1-(2-Methoxy-5-propylphenyl)ethanone

A suspension of 10.6 g of AlCl$_3$ in 150 mL of dichloromethane is cooled to −10° C. 5.7 mL of AcCl and 6 g of 4-propylanisole are added. The medium is stirred for 30 minutes at −10° C. and then poured into a beaker containing ice mixed with 35% HCl. After separation of the phases by settling, the aqueous phase is extracted 3 times with DCM and the combined organic phases are washed with water, with saturated NaCl solution, dried over MgSO$_4$ and then evaporated to give 7.86 g of a brown oil.

B) 2-Bromo-1-(2-methoxy-5-propylphenyl)ethanone

To a solution of 7.86 g of the compound obtained in the preceding step in 80 mL of methanol are added dropwise 2.46 mL of bromine diluted in 40 mL of methanol. The medium is stirred for 30 minutes at RT and then evaporated. The oil obtained is taken up in dichloromethane, washed 3 times with water and then dried over MgSO$_4$ and evaporated to give 11.25 g of a yellow oil.

C) 4-(2-Methoxy-5-propylphenyl)-1,3-thiazol-2-amine

To a solution of 8 g of the compound obtained in the preceding step in 60 mL of ethanol are added 4.94 g of thiourea. The medium is refluxed for 1 hour 30 minutes. The medium is then placed in a refrigerator for 12 hours and then filtered. The solid thus collected is rinsed with a small amount of cold ethanol and then with ether. The procedure is repeated a second time. The solid is suspended in a water/dichloromethane mixture and basified by addition of sodium hydroxide. The aqueous phase is extracted twice with dichloromethane. The combined organic phases are dried over MgSO$_4$ and then evaporated to give 4.89 g of a brown oil that crystallizes slowly (67%).

The mother liquors are evaporated and then stirred in a water/dichloromethane mixture and basified by addition of sodium hydroxide. The aqueous phase is extracted twice with dichloromethane. The combined organic phases are dried over MgSO$_4$ and then evaporated. The oil obtained is chromatographed on silica gel to give 580 mg of the expected product.

Yield (total): 75% m.p.=84° C.

Preparation I.26

4-(5-Cyclohexyl-2-methoxyphenyl)-5-fluorothiazol-2-yl amine

To a solution of 2.5 g of the compound obtained in Preparation I.3 described above in 30 mL of DMF are added, at 0° C., 3.4 g of Selectfluor® and the medium is stirred for 2 hours at RT. The medium is hydrolysed with 2 M ammonia in ethanol, concentrated and then diluted with water. The crude product is filtered off and the solid is taken up in DCM, washed with water and then with 1 M sodium hydroxide and with saturated NaCl solution. After drying of the organic phase over MgSO$_4$ and evaporation, the crude product is purified by flash chromatography.

600 mg of the expected compound are obtained in the form of a white powder.

m.p.=159° C.

Preparation I.27

4-(5-Propyl-2-methoxyphenyl)-5-fluorothiazol-2-ylamine

The compound is prepared according to Preparation I.26 starting with the compound from Preparation I.4 m.p.=107° C.

By working according to the above procedures, the compounds of formula (II) described in Table I below are prepared.

In the table that follows: Me=methyl, Et=ethyl, Pr=propyl, But=butyl, Hex=hexyl.

TABLE I

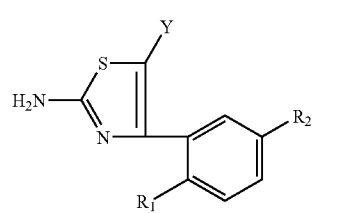

(II)

| Preparation No. | R$_1$ | R$_2$ | Y | Salt | m.p. (° C.) MH+ |
|---|---|---|---|---|---|
| I.1 | —OMe | —OPr | H | — | m.p. = 76 |
| I.2 | —OMe | —nBu | H | — | m.p. = 48 |
| I.2a | —OMe | —nBu | H | HBr | m.p. = 186 |
| I.3 | —OMe | 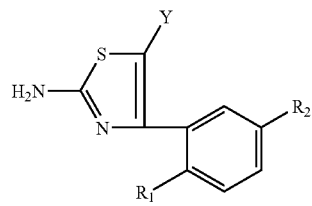 | H | — | m.p. = 113 |
| I.4 | —OMe | —nPr | H | — | m.p. = 84 |
| I.5 | —OEt | —Et | H | — | m.p. = 83 |
| I.6 | —OMe | —Et | H | — | m.p. = 100 |
| I.7 | —OEt | cyclohexyl | H | — | m.p. = 110 |
| I.8 | —OMe | cyclopentyl | H | — | m.p. = 110 |
| I.9 | —OEt | —nBu | H | — | m.p. = 65 |
| I.10 | —OMe | —CF$_3$ | H | — | m.p. = 144 |
| I.11 | —OMe | —iPr | H | — | m.p. = 109 |
| I.12 | —OMe | —Me | H | — | m.p. = 121 |
| I.13 | —O—CH$_2$—cyclopropyl | —nBu | H | — | m.p. = 59 |
| I.14 | —OMe | —CH(CH$_2$—CH$_3$)(CH$_2$—CH$_3$) | H | — | m.p. = 91-93 |
| I.16 | —Cl | —CF$_3$ | H | — | m.p. = 110 |
| I.17 | —OEt | —Me | H | — | m.p. = 124 |
| I.18 | —OMe | —CH(nPr)$_2$ | H | HCl | MH+ = 305.4 rt = 7.61 |

TABLE I-continued (II)

Structure: 2-amino-thiazole with Y at 5-position, and phenyl group at 4-position with R1 (ortho) and R2 (para/meta).

| Preparation No. | R₁ | R₂ | Y | Salt | m.p. (°C.) MH+ |
|---|---|---|---|---|---|
| I.19 | —OnPr | —nBu | H | — | m.p. = 63 |
| I.20 | —OMe | —nHex | H | — | m.p. = 43 |
| I.21 | —OEt | —nHex | H | — | m.p. = 75 |
| I.22 | —OMe | —CF₃CF₂ | H | — | m.p. = 125 |
| I.23 | —OEt | —CF₃CF₂ | H | — | MH⁺ = 338 rt = 7.88 |
| I.24 | —OEt | —nPr | H | — | m.p. = 87 |
| I.25 | —OEt | cyclopentyl | H | — | m.p. = 128 |
| I.26 | —OMe | cyclohexyl | F | — | m.p. = 159 |
| I.27 | —OMe | —Pr | F | — | m.p. = 107 |

Steps 1.1 and 1.2 of Example 1 described hereinbelow for the preparation of compound 120 illustrate the preparation of the compounds of formulae (IV) and (V).

By repeating the procedures described in steps 1.1 and 1.2 of Example 1, the compounds of formula (V') of Table II below may be prepared.

TABLE II (V')

| Compound | R₁ | R₂ | Y | n | m | A | m.p. (°C.), MH+, t and/or NMR |
|---|---|---|---|---|---|---|---|
| II.1 | 2-OCH₃ | 5-CyHex | H | 0 | 3 | —C(O)—O—C(CH₃)₃ | NMR5 |
| II.2 | 2-OCH₃ | 5-CyHex | H | 0 | 3 | H | NMR6 |
| II.3 | 2-OCH₃ | 5-CyHex | H | 2 | 2 | H | MH+ = 400 rt = 7.25 |
| II.4 (S) | 2-OCH₃ | 5-CyHex | H | 1 | 3 | —C(O)—O—C(CH₃)₃ | m.p. = 110 |
| II.5 | 2-OCH₃ | 5-CyHex | H | 1 | 3 | —C(O)—O—C(CH₃)₃ | m.p. = 107 |

TABLE II-continued (V')

[Structure: phenyl ring with R1, R2 substituents connected to thiazole ring (with Y, S, N) connected via NH-C(=O)-CH to a ring containing (CH2)m, (CH2)n, and N-A]

| Compound | R₁ | R₂ | Y | n | m | A | m.p. (° C.), MH+, t and/or NMR |
|---|---|---|---|---|---|---|---|
| II.6 (R) | 2-OCH₃ | 5-CyHex | H | 1 | 3 | -C(=O)-O-C(CH₃)₃ | m.p. = 73 |
| II.7 (R) | 2-OCH₃ | 5-CyHex | H | 1 | 3 | H | m.p. = 210 |
| II.8 (S) | 2-OCH₃ | 5-CyHex | H | 1 | 3 | H | m.p. = 202 |
| II.9 | 2-OCH₃ | 5-CyHex | H | 1 | 3 | H | m.p. = 236 |
| II.10 | 2-OCH₃ | 5-CyHex | H | 0 | 4 | -C(=O)-O-C(CH₃)₃ | m.p. = 110 |
| II.11 | 2-OCH₃ | 5-CyHex | H | 0 | 4 | H | m.p. = 164 |
| II.12 | 2-OCH₃ | 5-(CH₂)₃CH₃ | H | 1 | 3 | -C(=O)-O-C(CH₃)₃ | m.p. = 88 |
| II.13 | 2-OCH₃ | 5-CyPent | H | 1 | 3 | -C(=O)-O-C(CH₃)₃ | m.p. = 107 NMR1 |
| II.14 | 2-OCH₂CH₃ | 5-(CH₂)₃CH₃ | H | 1 | 3 | -C(=O)-O-C(CH₃)₃ | m.p. = 97 |
| II.15 | 2-OCH₃ | 5-CyPent | H | 1 | 3 | H | MH+ = 386 rt = 7.02 |
| II.16 | 2-OCH₃ | 5-(CH₂)₃CH₃ | H | 1 | 3 | H | MH+ = 374 rt = 7.01 |
| II.17 | 2-OCH₂CH₃ | 5-(CH₂)₃CH₃ | H | 1 | 3 | H | m.p. = 199 |
| II.18 | 2-OCH₃ | 5-(CH₂)₂CH₃ | H | 1 | 3 | -C(=O)-O-C(CH₃)₃ | NMR2 |

TABLE II-continued

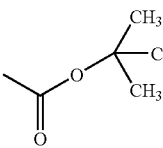

(V')

| Compound | R₁ | R₂ | Y | n | m | A | m.p. (° C.), MH+, t and/or NMR |
|---|---|---|---|---|---|---|---|
| II.19 (R) | 2-OCH$_3$ | 5-(CH$_2$)$_2$CH$_3$ | H | 1 | 3 | H | αD = −1.0 (1 = 1.66, MeOH), e.e = 99.9% rt = 12.66 |
| II.20 (S) | 2-OCH$_3$ | 5-(CH$_2$)$_2$CH$_3$ | H | 1 | 3 | H | αD = +0.78 (1 = 1.66, MeOH), e.e = 99.6% rt = 9.45 |
| II.21 | 2-OCH$_3$ | 5-(CH$_2$)$_2$CH$_3$ | H | 1 | 3 | H | NMR3 |
| II.22 | 2-OCH$_3$ | 5-O(CH$_2$)$_2$CH$_3$ | H | 1 | 3 | -C(CH$_3$)$_2$-O-C(O)- (tert-butyl ester group) | NMR4 |
| II.23 (R) | 2-OCH$_3$ | 5-O(CH$_2$)$_2$CH$_3$ | H | 1 | 3 | H | m.p. = 210 |
| II.24 (S) | 2-OCH$_3$ | 5-O(CH$_2$)$_2$CH$_3$ | H | 1 | 3 | H | m.p. = 208 |
| II.25 | 2-OCH$_3$ | 5-cyHex | H | 1 | 2 | -C(CH$_3$)$_2$-O-C(O)- | m.p. = 188 |
| II.26 | 2-OCH$_3$ | 5-cyHex | H | 1 | 2 | H | m.p. = 181 |
| II.27 | 2-OCH$_3$ | 5-cyHex | H | 2 | 2 | -C(CH$_3$)$_2$-O-C(O)- | m.p. = 193 |

NMR1
δ(ppm) = 1.21(s, 9H), 1.23–2.19(m, 12H), 2.73(m, 1H), 2.84-3.15(m, 2H), 3.77-4.12(m, 2H), 3.98(s, 3H), 7.05(d, 1H), 7.22(dd, 1H), 7.64(s, 1H), 8.01(d, 1H), 12.21(bs, 1H)

NMR2
See Example 2.1

NMR3
δ(ppm) = 0.81(t, 3H), 1.21-1.90(m, 6H), 2.38-3.02(m, 7H), 3.81(s, 3H), 6.99(d, 1H), 7.04(dd, 1H), 7.57(s, 1H), 7.84 (d, 1H), 12.20(bs, 1H)

NMR4
δ(ppm) = 0.84(t, 3H), 1.22(s, 9H), 1.58-1.78(m, 4H), 1.81-1.90(m, 2H), 2.58(m, 1H), 2.80(m, 3H), 3.0-3.15(m, 1H), 3.59-3.97(m, 4H), 3.92(s, 3H), 6.79(dd, 1H), 6.98(d, 1H), 7.58(d, 1H), 7.60(s, 1H), 12.17(bs, 1H)

NMR5
δ(ppm) = 1.17(s, 9H), 1.20-2.21(m, 13H), 2.16(m, 1H), 2.39(m, 1H), 3.18-3.40(m, 2H), 3.89(s, 3H), 4.26(m, 1H), 6.92(d, 1H), 7.04(dd, 1H), 7.57(s, 1H), 7.84(d, 1H), 12.21(bs 1H)

NMR6
δ(ppm) = 1.20-1.28(m, 1H), 1.30-1.49(m, 4H), 1.66-1.75(m, 3H), 1.76-1.85(m, 5H), 2.01-2.17(m, 1H), 2.47-2.51(m, 1H), 2.80-2.97(m, 2H), 3.84(m, 1H), 3.90(s, 3H), 6.99(d, 1H), 7.15(dd, 1H), 7.62(s, 1H), 7.94(d, 1H)

The examples that follow illustrate the invention without limiting it.

EXAMPLE 1

(compound 120) 1-(Pyrazine-2-carbonyl)piperidine-4-carboxylic acid [4-(5-cyclohexyl-2-methoxyphenyl)thiazol-2-yl]amide Compound of general formula (I) in which:
$R_1$=2-OMe; $R_2$=5-CyHex; m=2; n=2; p=0;

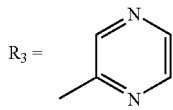

1.1. Preparation of tert-butyl 4-[4-(5-cyclohexyl-2-methoxyphenyl)thiazol-2-ylcarbamoyl]piperidine-1-carboxylate (compound II.27)

1.68 g of BOP, 0.75 g of Boc-isonipecotic acid and then 1.41 mL of DIPEA are added, at a temperature of 0° C., to a solution of 1 g of 4-(2-methoxy-5-cyclohexylphenyl)-1,3-thiazol-2-amine, obtained in preparation I.3, in 6 mL of acetonitrile. The medium is stirred at room temperature for 24 hours and then filtered. The solid thus obtained is rinsed with acetonitrile and then dried. 1.13 g of a white solid are thus obtained.

m.p.=193° C.

1.2. Preparation of piperidine-4-carboxylic acid [4-(5-cyclohexyl-2-methoxyphenyl)thiazol-2-yl]amide (compound II.3)

A solution of 1.13 g of the compound prepared in step 1.1 in 10 mL of a 4 M solution of HCl in ioxane is stirred for 30 minutes at room temperature. The medium is diluted with ethyl ether and then filtered. The solid thus obtained is rinsed with ether and then dried to give 1.01 g of a white solid.

$MH^+$=400 at rt=7.25 min.

1.3. Preparation of 1-(pyrazine-2-carbonyl)piperidine-4-carboxylic acid [4-(5-cyclohexyl-2-methoxyphenyl)thiazol-2-yl]amide 0.32 g of BOP, 0.08 g of pyrazinecarboxylic acid and then 0.37 mL of DIPEA are added, at a temperature of 0° C., to a solution of 0.25 g of the compound prepared in step 1.2 in 3 mL of acetonitrile. The medium is stirred at room temperature for 12 hours and then concentrated. The medium is taken up in EtOAc and washed 3 times with 10% $Na_2CO_3$ solution and then with saturated NaCl solution. After drying over $MgSO_4$, the solution is concentrated and then purified by flash chromatography to give 0.23 g of a dark yellow solid.

m.p.=129° C.

EXAMPLE 2

(compound 93) (S)-1-(Pyridine-2-carbonyl)piperidine-3-carboxylic acid [4-(2-methoxy-5-propylphenyl)thiazol-2-yl]amide hydrochloride Compound of general formula (I) in which:
$R_1$=2-OMe; $R_2$=5-n-propyl; m=3; n=1; p=0;

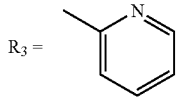

2.1. Preparation of tert-butyl (S)-3-[4-(2-methoxy-5-propylphenyl)thiazol-2-ylcarbamoyl]piperidine-1-carboxylate ((S) enantiomer of compound II.18)

0.5 g of TBTU, 0.1 g of HOBT, 0.35 g of (S)-N-Boc-nipecotic acid and then 0.3 mL of DIPEA are added, at a temperature of 0° C., to a solution of 0.5 g of 4-(2-methoxy-5-propylphenyl)-1,3-thiazol-2-amine, obtained in preparation I.4, in 4 mL of DMF. The medium is stirred at room temperature for 3 hours and then diluted with EtOAc and washed 4 times with 10% $Na_2CO_3$ solution and then with saturated NaCl solution. After drying over $MgSO_4$, the solution is concentrated and then purified by flash chromatography to give 0.56 g of a white solid.

NMR δ (ppm)=0.77 (t, 3H); 1.22 (s, 9H); 1.24-1.88 (m, 7H); 2.43 (m, 2H); 2.55 (m, 2H); 2.79 (m, 2H); 3.6-3.75 (m, 2H); 3.78 (s, 3H); 6.92 (d, 1H); 7.04 (d.d, 1H); 7.54 (s, 1H); 7.82 (d, 1H); 12.19 (bs, 1H).

2.2. Preparation of (S)-piperidine-3-carboxylic acid [4-(2-methoxy-5-propylphenyl)thiazol-2-yl]amide (compound II.20)

1 mL of TFA is added, at a temperature of 0° C., to a solution of 0.56 g of the compound prepared in step 2.1, in 3 mL of DCM. The medium is stirred for 2 hours at room temperature. The medium is concentrated and then taken up in 20 mL of DCM and washed 3 times with 10% $Na_2CO_3$ solution and then with saturated NaCl solution. The organic phase is evaporated to give 0.36 g of a white solid.

$α_D$=+0.78 (c=1.66 in an $MeOH/CHCl_3$ mixture (1/1))

2.3. Preparation of (S)-1-(pyridine-2-carbonyl)piperidine-3-carboxylic acid [4-(2-methoxy-5-propylphenyl)thiazol-2-yl]amide hydrochloride 0.071 g of picolinoyl chloride and then 0.12 mL of DIPEA are added, at a temperature of 0° C., to a solution of 0.12 g of the compound prepared in step 2.2, in 1 mL of acetonitrile. The medium is stirred until it has returned to room temperature. After 1 hour at room temperature, the medium is hydrolysed and then diluted with EtOAc and washed with 10% $Na_2CO_3$ solution and then with saturated NaCl solution. After drying over $MgSO_4$, the solution is concentrated. The crude product obtained is taken up in DCM. The hydrochloride is formed by addition of 2 M hydrochloric ethyl ether. The solid obtained is filtered off and rinsed with ethyl ether. The free base is obtained by treatment with 1 M sodium hydroxide and is then extracted into DCM and the organic phase is dried over $MgSO_4$ and then evaporated. The free base is taken up in DCM. The hydrochloride is obtained by addition of 2 M hydrochloric ethyl ether. The solid obtained is filtered off, rinsed with ethyl ether and then dried to give 91 mg of a white solid.

m.p.=162° C.

EXAMPLE 3

(compound 105) (R,S)-1-(1-oxypyridine-2-carbonyl)pyrrolidine-3-carboxylic acid [4-(5-cyclohexyl-2-methoxyphenyl)thiazol-2-yl]amide Compound of general formula (I) in which:
$R_1$=2-OMe; $R_2$=5-CyHex; m=2; n=1; p=0;

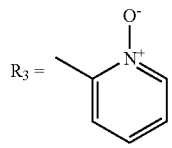

3.1. Preparation of tert-butyl (R,S)-3-[4-(5-cyclohexyl-2-methoxyphenyl)thiazol-2-ylcarbamoyl]-pyrrolidine-1-carboxylate (compound II.25)

2.1 g of BOP, 0.9 g of 3-Boc-pyrrolidinecarboxylic acid and then 1.2 mL of DIPEA are added, at a temperature of 0° C., to a solution of 1 g of 4-(2-methoxy-5-cyclohexylphenyl)-1,3-thiazol-2-amine, obtained in preparation I.3, in 6 mL of acetonitrile. The medium is stirred at room temperature for 12 hours and then filtered. The solid thus obtained is rinsed with acetonitrile and then dried to give 1.37 g of a white solid.
m.p.=188° C.

3.2. Preparation of (R,S)-pyrrolidine-3-carboxylic acid [4-(5-cyclohexyl-2-methoxyphenyl)thiazol-2-yl]amide (compound II.26)

A solution of 1.35 g of the compound prepared in step 3.1, in 40 mL of a 4 M solution of HCl in dioxane, is stirred for 2 hours at room temperature. The medium is diluted with ethyl ether and then filtered. The solid thus obtained is rinsed with ether and then taken up in a DCM/saturated $Na_2CO_3$ solution mixture (1/1). The aqueous phase is extracted with DCM, washed with water and then dried over $MgSO_4$ and evaporated to give 1.02 g of a white solid.
m.p.=181° C.

3.3. Preparation of (R,S)-1-(1-oxypyridine-2-carbonyl)pyrrolidine-3-carboxylic acid [4-(5-cyclohexyl-2-methoxyphenyl)thiazol-2-yl]amide 0.108 g of picolinic acid N-oxide, 0.4 g of BOP and then 0.23 mL of DIPEA are added, at 0° C., to a solution of 0.25 g of the compound prepared in step 3.2, in 3 mL of acetonitrile. The medium is stirred for 12 hours at room temperature and then filtered. The solid collected is rinsed with acetonitrile and then purified by flash chromatography to give 0.23 g of the expected compound.
m.p.=161° C.

By following these procedures starting with (R)-3-Boc-pyrrolidinecarboxylic acid, compound 239 is obtained: m.p.=155° C., $\alpha_D$=−32 (c=1.6, $CHCl_3$), optical purity=96.4% (HPLC on Chiralpak AD-H (250 mm×4.6), technique: SFC, mobile phase: $CO_2$/isopropanol+0.5% IPA 70/30 2 ml/min, 200 bar, 30° C., UV detection at 254 nm at rt=12.56 min).

By following these procedures starting with (S)-3-Boc-pyrrolidinecarboxylic acid, compound 240 is obtained: m.p.=157° C., $\alpha_D$=+30 (c=1.6, $CHCl_3$), optical purity=97.6% (HPLC on Chiralpak AD-H (250 mm×4.6), technique: SFC, mobile phase: $CO_2$/isopropanol+0.5% IPA 70/30 2 ml/min, 200 bar, 30° C., UV detection at 254 nm at rt=13.99 min).

EXAMPLE 4

(compound 99) (R,S)-1-(pyrazine-2-carbonyl)piperidine-3-carboxylic acid [4-(5-butyl-2-ethoxyphenyl)thiazol-2-yl]amide Compound of general formula (I) in which:
$R_1$=2-ethoxy; $R_2$=5-butyl; m=3; n=1; p=0;

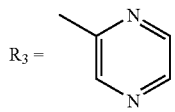

4.1. Preparation of (R,S)-1-(pyrazine-2-carbonyl)piperidine-3-carboxylic acid 7.7 mL of BSA are added to a solution of 2.1 g of nipecotic acid in 50 mL of DCM. The mixture is left for 1 hour at room temperature. 2.1 g of pyrazinecarboxylic acid chloride, obtained by treating pyrazinecarboxylic acid with $SOCl_2$ (Advanced in Organic Chemistry, J. March, $3^{rd}$ Edition, Wiley Intersciences, p. 523 and cited refs.) are then added, at a temperature of 0° C. The medium is stirred at room temperature for 12 hours and is then concentrated. The crude product is taken up in a water/methanol mixture and then diluted with ethyl ether. After trituration, a solid is collected by filtration. It is taken up in DCM. After filtration, the filtrate is evaporated. The solid thus obtained is taken up in DCM. After filtration, the filtrate is evaporated to give 2.1 g of a white solid.
MH+=234 at rt=3.91 min

4.2. Preparation of (R,S)-1-(pyrazine-2-carbonyl)piperidine-3-carboxylic acid [4-(5-butyl-2-ethoxyphenyl)thiazol-2-yl]amide 0.3 g of 4-(2-ethoxy-5-butylphenyl)-1,3-thiazol-2-amine, obtained in preparation I.9, 0.67 g of BOP and then 0.76 mL of DIPEA are added, at a temperature of 0° C., to a solution of 0.40 g of the compound prepared in step 4.1, in 3 mL of acetonitrile. The medium is stirred at room temperature for 12 hours and then filtered. The solid thus obtained is rinsed with acetonitrile and then dried to give 0.34 g of a white solid.
m.p.=182° C.

Table III below illustrates the chemical structures and the physical properties of a number of examples of compounds according to the invention. In this table:
m.p.=melting point, in degrees Celsius (° C.),
MH+=mass spectrometry,
rt=retention time, in minutes (min.),
CyHex represents a cyclohexyl group, and CyPent represents a cyclopentyl group,
in the "salts" column, "-" represents a compound in free base form, whereas "HCl" represents a compound in its hydrochloride form,
(+) indicates that the compound is a dextrorotatory enantiomer, and (−) indicates a laevorotatory enantiomer,
(R) indicates that the compound is an R enantiomer, and (S) indicates an S enantiomer.

TABLE III
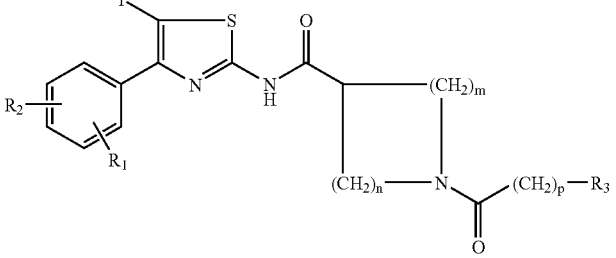
(I)
| N° | R₁ | R₂ | R₃ | Y | p | n | m | salt | m.p. and/or MH+, rt |
|---|---|---|---|---|---|---|---|---|---|
| 1 | 2-OCH₃ | 5-O(CH₂)₂CH₃ | 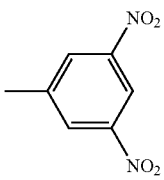 | H | 0 | 1 | 3 | — | MH+ = 570, rt = 10.37 |
| 2 | 2-OCH₃ | 5-O(CH₂)₂CH₃ | 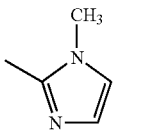 | H | 0 | 1 | 3 | — | MH+ = 516, rt = 10.31 |
| 3 (S) | 2-OCH₃ | 5-CyHex | 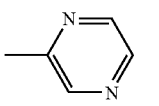 | H | 0 | 1 | 3 | — | m.p. = 118 |
| 4 (S) | 2-OCH₃ | 5-CyHex | 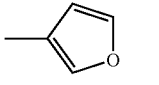 | H | 0 | 1 | 3 | — | MH+ = 506, rt = 10.21 |
| 5 | 2-OCH₃ | 5-O(CH₂)₂CH₃ | 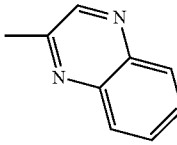 | H | 0 | 1 | 3 | — | MH+ = 470, rt = 9.64 |
| 6 | 2-OCH₃ | 5-O(CH₂)₂CH₃ | 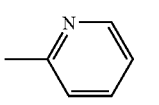 | H | 0 | 1 | 3 | — | MH+ = 532, rt = 9.97 |
| 7 (S) | 2-OCH₃ | 5-CyHex | 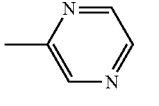 | H | 0 | 1 | 3 | — | MH+ = 505, rt = 10.61 m.p. = 142 |
| 8 | 2-OCH₃ | 5-O(CH₂)₂CH₃ | 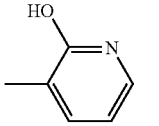 | H | 0 | 1 | 3 | — | MH+ = 482, rt = 9.05 |
| 9 | 2-OCH₃ | 5-O(CH₂)₂CH₃ |  | H | 0 | 1 | 3 | — | MH+ = 497, rt = 8.26 |

TABLE III-continued

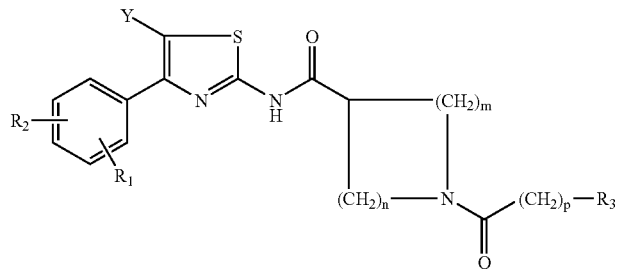

(I)

| N° | R₁ | R₂ | R₃ | Y | p | n | m | salt | m.p. and/or MH+, rt |
|---|---|---|---|---|---|---|---|---|---|
| 10 | 2-OCH₃ | 5-O(CH₂)₂CH₃ | 5-chloro-1,4-dimethyl-pyrazol-3-yl | H | 0 | 1 | 3 | — | MH+ = 518, rt = 9.39 |
| 11 | 2-OCH₃ | 5-(CH₂)₃CH₃ | 5-bromo-2-methyl-furan-3-yl | H | 0 | 1 | 3 | — | MH+ = 546, rt = 11.13 |
| | 2-OCH₃ | 5-CyHex | 6-chloro-2-methyl-pyridin-3-yl | H | 0 | 1 | 3 | — | MH+ = 539, rt = 11.24 |
| 13 | 2-OCH₃ | 5-CyHex | 3,6-dichloro-2-methyl-pyridin-4-yl | H | 0 | 1 | 3 | — | MH+ = 573, rt = 11.49 |
| | 2-OCH₃ | 5-CyHex | isoquinolin-1-ylmethyl | H | 0 | 1 | 3 | — | MH+ = 555, rt = 11.13 |
| 15 | 2-OCH₃ | 5-CyHex | 6-chloro-5-methyl-pyridin-3-yl | H | 0 | 1 | 3 | — | MH+ = 538, rt = 11.05 |
| 16 | 2-OCH₃ | 5-CyHex | 2-chloro-3-methyl-pyridin-4-yl | H | 0 | 1 | 3 | — | MH+ = 539, rt = 10.84 |
| 17 | 2-OCH₃ | 5-CyHex | 3,5-dimethyl-pyridin-4-yl | H | 0 | 1 | 3 | — | MH+ = 519, rt = 9.96 |

TABLE III-continued
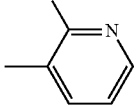
(I)
| N° | R₁ | R₂ | R₃ | Y | p | n | m | salt | m.p. and/or MH+, rt |
|---|---|---|---|---|---|---|---|---|---|
| 18 | 2-OCH₃ | 5-CyHex | 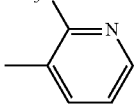 | H | 0 | 1 | 3 | — | MH+ = 523, rt = 10.81 |
| 19 | 2-OCH₃ | 5-CyHex | 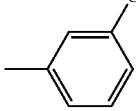 | H | 0 | 1 | 3 | — | MH+ = 535, rt = 10.92 |
| 20 | 2-OCH₃ | 5-CyHex | 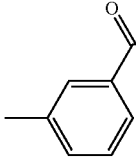 | H | 0 | 1 | 3 | — | MH+ = 529, rt = 11.08 |
| 21 | 2-OCH₃ | 5-CyHex | 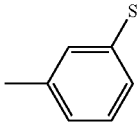 | H | 0 | 1 | 3 | — | MH+ = 546, rt = 10.99 |
| 22 | 2-OCH₃ | 5-CyHex | 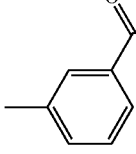 | H | 0 | 1 | 3 | — | MH+ = 582, rt = 10.61 |
|  | 2-OCH₃ | 5-CyHex | 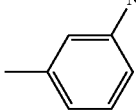 | H | 0 | 1 | 3 | — | MH+ = 562, rt = 11.28 |
| 24 | 2-OCH₃ | 5-CyHex | 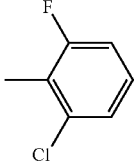 | H | 0 | 1 | 3 | — | MH+ = 549, rt = 11.29 |
| 25 | 2-OCH₃ | 5-CyHex |  | H | 0 | 1 | 3 | — | MH+ = 556, rt = 11.74 |

TABLE III-continued
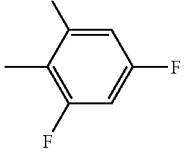
(I)
| N° | R₁ | R₂ | R₃ | Y | p | n | m | salt | m.p. and/or MH+, rt |
|---|---|---|---|---|---|---|---|---|---|
| 26 | 2-OCH₃ | 5-CyHex | 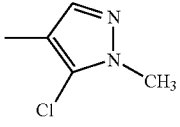 | H | 0 | 1 | 3 | — | MH+ = 558, rt = 11.63 |
| 27 | 2-OCH₃ | 5-CyHex | 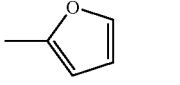 | H | 0 | 1 | 3 | — | MH+ = 543, rt = 10.67 |
| 28 | 2-OCH₃ | 5-CyHex | 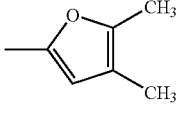 | H | 0 | 1 | 3 | — | MH+ = 494, rt = 11.00 |
| 29 | 2-OCH₃ | 5-CyHex | 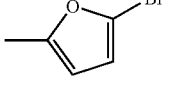 | H | 0 | 1 | 3 | — | MH+ = 522, rt = 11.61 |
| 30 | 2-OCH₃ | 5-CyHex | 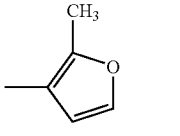 | H | 0 | 1 | 3 | — | MH+ = 572, rt = 11.57 |
| 31 | 2-OCH₃ | 5-CyHex | 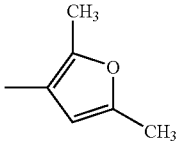 | H | 0 | 1 | 3 | — | MH+ = 508, rt = 11.20 |
| 32 | 2-OCH₃ | 5-CyHex | 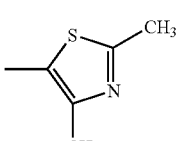 | H | 0 | 1 | 3 | — | MH+ = 522, rt = 11.57 |
| 33 | 2-OCH₃ | 5-CyHex | 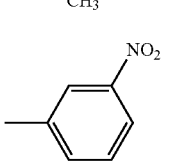 | H | 0 | 1 | 3 | — | MH+ = 539, rt = 10.70 |
| 34 | 2-OCH₃ | 5-O(CH₂)₂CH₃ |  | H | 0 | 1 | 3 | — | MH+ = 525, rt = 10.12 |

TABLE III-continued

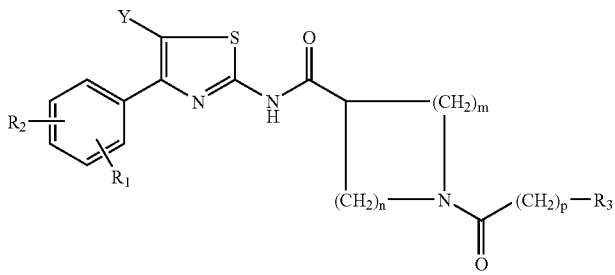
(I)

| N° | R₁ | R₂ | R₃ | Y | p | n | m | salt | m.p. and/or MH+, rt |
|---|---|---|---|---|---|---|---|---|---|
| 35 | 2-OCH₃ | 5-(CH₂)₃CH₃ | 6-chloro-2-pyridyl | H | 0 | 1 | 3 | — | MH+ = 513, rt = 10.79 |
| 36 | 2-OCH₃ | 5-(CH₂)₃CH₃ | 3-cyanophenyl | H | 0 | 1 | 3 | — | MH+ = 503, rt = 10.64 |
| 37 | 2-OCH₃ | 5-(CH₂)₃CH₃ | 3-acetylphenyl | H | 0 | 1 | 3 | — | MH+ = 520, rt = 10.55 |
| 38 | 2-OCH₃ | 5-(CH₂)₃CH₃ | 3-nitrophenyl | H | 0 | 1 | 3 | — | MH+ = 523, rt = 10.86 |
| 39 | 2-OCH₃ | 5-(CH₂)₃CH₃ | 2-fluoro-6-chlorophenyl | H | 0 | 1 | 3 | — | MH+ = 530, rt = 11.32 |
| 40 | 2-OCH₃ | 5-(CH₂)₃CH₃ | 2,3,5-trifluorophenyl | H | 0 | 1 | 3 | — | MH+ = 532, rt = 11.20 |
| 41 | 2-OCH₃ | 5-(CH₂)₃CH₃ | 1,3,5-trimethylpyrazol-4-yl | H | 0 | 1 | 3 | — | MH+ = 496, rt = 10.28 |
| 42 | 2-OCH₃ | 5-(CH₂)₃CH₃ | 5-chloro-1,4-dimethylpyrazol-3-yl | H | 0 | 1 | 3 | — | MH+ = 516, rt = 10.20 |

TABLE III-continued
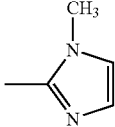
(I)
| N° | R₁ | R₂ | R₃ | Y | p | n | m | salt | m.p. and/or MH+, rt |
|---|---|---|---|---|---|---|---|---|---|
| 43 | 2-OCH₃ | 5-(CH₂)₃CH₃ | 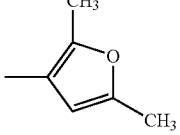 | H | 0 | 1 | 3 | — | MH+ = 482, rt = 9.24 |
| 44 | 2-OCH₃ | 5-(CH₂)₃CH₃ | 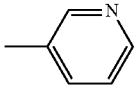 | H | 0 | 1 | 3 | — | MH+ = 496, rt = 11.13 |
| 45 | 2-OCH₃ | 5-(CH₂)₃CH₃ | 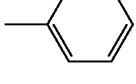 | H | 0 | 1 | 3 | — | MH+ = 479, rt = 9.49 |
| 46 | 2-OCH₃ | 5-(CH₂)₃CH₃ | 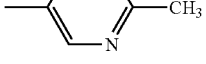 | H | 0 | 1 | 3 | — | MH+ = 479, rt = 10.12 |
| 47 | 2-OCH₃ | 5-(CH₂)₃CH₃ | 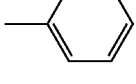 | H | 0 | 1 | 3 | — | MH+ = 493, rt = 9.12 |
| 48 | 2-OCH₃ | 5-(CH₂)₃CH₃ | 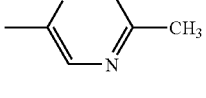 | H | 1 | 1 | 3 | — | MH+ = 493, rt = 8.50 |
| 49 | 2-OCH₃ | 5-(CH₂)₃CH₃ | 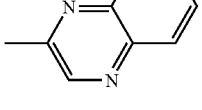 | H | 0 | 1 | 3 | — | MH+ = 494, rt = 10.09 |
| 50 | 2-OCH₃ | 5-CyHex | 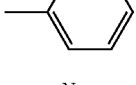 | H | 0 | 1 | 3 | — | MH+ = 556, rt = 11.23 |
| 51 | 2-OCH₃ | 5-CyHex | 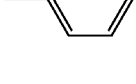 | H | 0 | 1 | 3 | — | MH+ = 505, rt = 9.91 |
| 52 | 2-OCH₃ | 5-CyHex |  | H | 0 | 1 | 3 | — | MH+ = 505, rt = 10.62 |

TABLE III-continued (I)

| N° | R₁ | R₂ | R₃ | Y | p | n | m | salt | m.p. and/or MH+, rt |
|---|---|---|---|---|---|---|---|---|---|
| 53 | 2-OCH₃ | 5-CyHex | 3,5-dinitrophenyl | H | 0 | 1 | 3 | — | MH+ = 594, rt = 11.46 |
| 54 | 2-OCH₃ | 5-CyHex | 2,6-difluorophenyl | H | 0 | 1 | 3 | — | MH+ = 540, rt = 11.49 |
| 55 | 2-OCH₃ | 5-CyHex | 3-furyl | H | 0 | 1 | 3 | — | MH+ = 494, rt = 10.92 |
| 56 | 2-OCH₃ | 5-CyHex | 2-methyl-3-pyridyl | H | 0 | 1 | 3 | — | MH+ = 519, rt = 9.28 |
| 57 | 2-OCH₃ | 5-CyHex | 5-bromo-3-pyridyl | H | 0 | 1 | 3 | — | MH+ = 584, rt = 11.06 |
| 58 | 2-OCH₃ | 5-CyHex | 6-hydroxy-3-pyridyl | H | 0 | 1 | 3 | — | MH+ = 521, rt = 9.44 |
| 59 | 2-OCH₃ | 5-CyHex | 6-methyl-3-pyridyl | H | 0 | 1 | 3 | — | MH+ = 519, rt = 9.51 |
| 60 | 2-OCH₃ | 5-CyHex | 2-pyridyl | H | 1 | 1 | 3 | — | MH+ = 519, rt = 8.90 |
| 61 | 2-OCH₃ | 5-CyHex | 3-pyridyl | H | 2 | 1 | 3 | — | MH+ = 533, rt = 8.16 |

TABLE III-continued
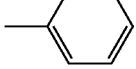
(I)
| N° | R₁ | R₂ | R₃ | Y | p | n | m | salt | m.p. and/or MH+, rt |
|---|---|---|---|---|---|---|---|---|---|
| 62 | 2-OCH₃ | 5-CyHex | 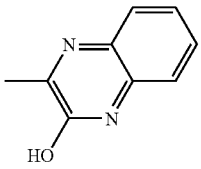 | H | 1 | 1 | 3 | — | MH+ = 519, rt = 8.37 |
| 63 | 2-OCH₃ | 5-CyHex | 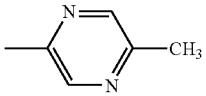 | H | 0 | 1 | 3 | — | MH+ = 572, rt = 10.34 |
| 64 | 2-OCH₃ | 5-CyHex | 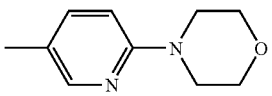 | H | 0 | 1 | 3 | — | MH+ = 520, rt = 10.56 |
| 65 | 2-OCH₃ | 5-CyHex | 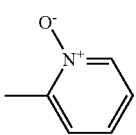 | H | 0 | 1 | 3 | — | MH+ = 590, rt = 10.20 |
| 66 | 2-OCH₂CH₃ | 5-CH₂CH₃ | 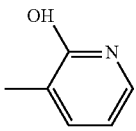 | H | 0 | 1 | 3 | — | MH+ = 481, rt = 8.66 |
| 67 | 2-OCH₂CH₃ | 5-CH₂CH₃ | 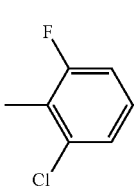 | H | 0 | 1 | 3 | — | MH+ = 480, rt = 8.59 |
| 68 | 2-OCH₂CH₃ | 5-CH₂CH₃ | 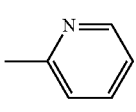 | H | 0 | 1 | 3 | — | MH+ = 516, rt = 10.90 |
| 69 | 2-OCH₂CH₃ | 5-CH₂CH₃ | 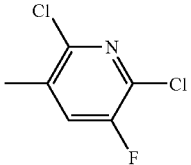 | H | 0 | 1 | 3 | — | MH+ = 465, rt = 9.64 |
| 70 | 2-OCH₂CH₃ | 5-CH₂CH₃ | | H | 0 | 1 | 3 | — | MH+ = 551, rt = 11.02 |

TABLE III-continued
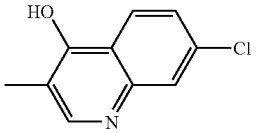
(I)
| N° | R₁ | R₂ | R₃ | Y | p | n | m | salt | m.p. and/or MH+, rt |
|---|---|---|---|---|---|---|---|---|---|
| 71 | 2-OCH₂CH₃ | 5-CH₂CH₃ | 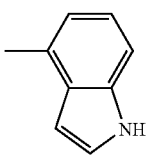 | H | 0 | 1 | 3 | — | MH+ = 566, rt = 9.56 |
| 72 | 2-OCH₂CH₃ | 5-CH₂CH₃ | 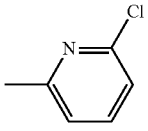 | H | 0 | 1 | 3 | — | MH+ = 503, rt = 10.12 |
| 73 | 2-OCH₃ | 5-O(CH₂)₂CH₃ | 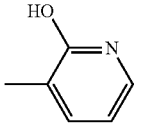 | H | 0 | 1 | 3 | — | MH+ = 515, rt = 9.99 |
| 74 | 2-OCH₃ | 5-(CH₂)₃CH₃ | 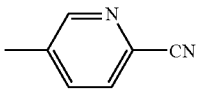 | H | 0 | 1 | 3 | — | MH+ = 495, rt = 9.03 |
| 75 | 2-OCH₃ | 5-CyHex | 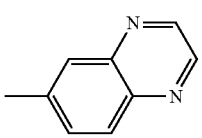 | H | 0 | 1 | 3 | — | MH+ = 530, rt = 10.8 |
| 76 | 2-OCH₃ | 5-CyHex | 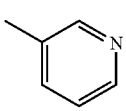 | H | 0 | 1 | 3 | — | MH+ = 556, rt = 10.49 |
| 77 | 2-OCH₃ | 5-O(CH₂)₂CH₃ | 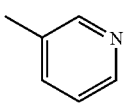 | H | 0 | 1 | 3 | — | m.p. = 192 |
| 78 (−) | 2-OCH₃ | 5-O(CH₂)₂CH₃ | 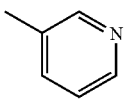 | H | 0 | 1 | 3 | — | m.p. = 104 |
| 79 (+) | 2-OCH₃ | 5-O(CH₂)₂CH₃ |  | H | 0 | 1 | 3 | — | m.p. = 104 |

TABLE III-continued (I)

| N° | R₁ | R₂ | R₃ | Y | p | n | m | salt | m.p. and/or MH+, rt |
|---|---|---|---|---|---|---|---|---|---|
| 80 (−) | 2-OCH₃ | 5-O(CH₂)₂CH₃ | 2-pyridyl | H | 0 | 1 | 3 | — | m.p. = 90<br>mH+ = 482,<br>rt = 8.61 |
| 81 (+) | 2-OCH₃ | 5-O(CH₂)₂CH₃ | 2-pyridyl | H | 0 | 1 | 3 | — | m.p. = 90<br>MH+ = 482,<br>rt = 8.63 |
| 82 | 2-OCH₃ | 5-O(CH₂)₂CH₃ | 2-pyridyl | H | 0 | 1 | 3 | — | m.p. = 52 |
| 83 (+) | 2-OCH₃ | 5-O(CH₂)₂CH₃ | 2,6-dichloro-3-methylphenyl | H | 0 | 1 | 3 | — | m.p. = 241 |
| 84 | 2-OCH₃ | 5-O(CH₂)₂CH₃ | 2,6-dichloro-3-methylphenyl | H | 0 | 1 | 3 | — | m.p. = 240 |
| 85 (−) | 2-OCH₃ | 5-O(CH₂)₂CH₃ | 2,6-dichloro-3-methylphenyl | H | 0 | 1 | 3 | — | m.p. = 241 |
| 86 | 2-OCH₃ | 5-(CH₂)₂CH₃ | 3-pyridyl | H | 0 | 1 | 3 | — | m.p. = 212 |
| 87 | 2-OCH₃ | 5-(CH₂)₂CH₃ | 2-pyridyl | H | 0 | 1 | 3 | — | m.p. = 104 |
| 88 (S) | 2-OCH₃ | 5-CyPent | 3-pyridyl | H | 0 | 1 | 3 | HCl | m.p. = 176 |

TABLE III-continued
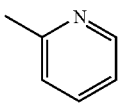
(I)
| N° | R₁ | R₂ | R₃ | Y | p | n | m | salt | m.p. and/or MH+, rt |
|---|---|---|---|---|---|---|---|---|---|
| 89 (S) | 2-OCH₃ | 5-CyPent | 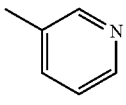 | H | 0 | 1 | 3 | HCl | m.p. = 162 |
| 90 (R) | 2-OCH₃ | 5-CyPent | 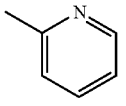 | H | 0 | 1 | 3 | HCl | m.p. = 178.9 |
| 91 (R) | 2-OCH₃ | 5-CyPent | 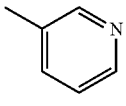 | H | 0 | 1 | 3 | HCl | m.p. = 161 |
| 92 (S) | 2-OCH₃ | 5-(CH₂)₂CH₃ | 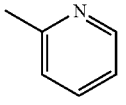 | H | 0 | 1 | 3 | HCl | m.p. = 170 |
| 93 (S) | 2-OCH₃ | 5-(CH₂)₂CH₃ | 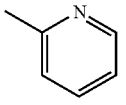 | H | 0 | 1 | 3 | HCl | m.p. = 162.4 |
| 94 (R) | 2-OCH₃ | 5-(CH₂)₂CH₃ | 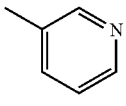 | H | 0 | 1 | 3 | HCl | m.p. = 156 |
| 95 | 2-OCH₃ | 5-CyPent | 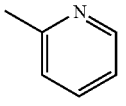 | H | 0 | 1 | 3 | HCl | MH+ = 492, rt = 8.15 |
| 96 | 2-OCH₃ | 5-CyPent | 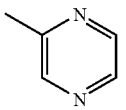 | H | 0 | 1 | 3 | HCl | m.p. = 166.7 |
| 97 | 2-OCH₃ | 5-CyHex | 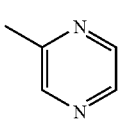 | H | 0 | 1 | 3 | — | m.p. = 206.2 |
| 98 | 2-OCH₂CH₃ | 5-CyHex | 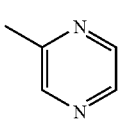 | H | 0 | 1 | 3 | — | m.p. = 186.1 |

TABLE III-continued
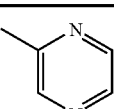
(I)
| N° | R₁ | R₂ | R₃ | Y | p | n | m | salt | m.p. and/or MH+, rt |
|---|---|---|---|---|---|---|---|---|---|
| 99 | 2-OCH₂CH₃ | 5-(CH₂)₃CH₃ | 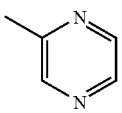 | H | 0 | 1 | 3 | — | m.p. = 182 |
| 100 | 2-OCH₃ | 5-CyPent | 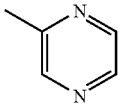 | H | 0 | 1 | 3 | — | m.p. = 192.8 |
| 101 | 2-OCH₃ | 5-CyHex | 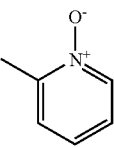 | H | 0 | 1 | 3 | — | m.p. = 179.4 |
| 102 | 2-OCH₃ | 5-CyHex | 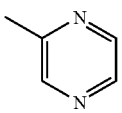 | H | 0 | 1 | 3 | — | m.p. = 188.3 |
| 103 | 2-OCH₃ | 5-(CH₂)₃CH₃ | 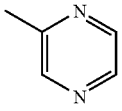 | H | 0 | 1 | 3 | — | m.p. = 106 |
| 104 | 2-OCH₃ | 5-CyHex | 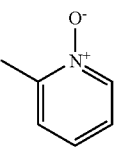 | H | 0 | 1 | 2 | — | m.p. = 115 |
| 105 | 2-OCH₃ | 5-CyHex | 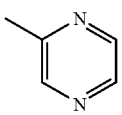 | H | 0 | 1 | 2 | — | m.p. = 161 |
| 106 (R) | 2-OCH₃ | 5-CyHex | 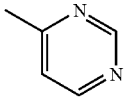 | H | 0 | 1 | 3 | — | m.p. = 119.8 |
| 107 | 2-OCH₃ | 5-CyHex | 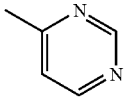 | H | 0 | 1 | 3 | — | m.p. = 115.8 |

TABLE III-continued
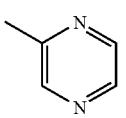
(I)
| N° | R₁ | R₂ | R₃ | Y | p | n | m | salt | m.p. and/or MH+, rt |
|---|---|---|---|---|---|---|---|---|---|
| 108 (S) | 2-OCH₃ | 5-CyHex | 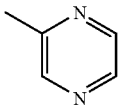 | H | 0 | 1 | 3 | — | m.p. = 115 |
| 109 | 2-OCH₃ | 5-CyHex | 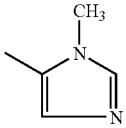 | H | 0 | 0 | 4 | — | m.p. = 109 |
| 110 | 2-OCH₃ | 5-CyHex | 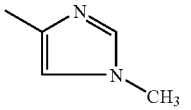 | H | 0 | 1 | 3 | — | m.p. = 228 |
| 111 | 2-OCH₃ | 5-CyHex | 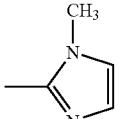 | H | 0 | 1 | 3 | — | m.p. = 237 |
| 112 | 2-OCH₃ | 5-CyHex | 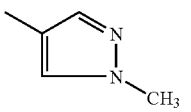 | H | 0 | 1 | 3 | — | m.p. = 113 |
| 113 | 2-OCH₃ | 5-CyHex | 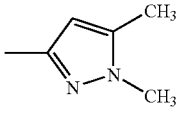 | H | 0 | 1 | 3 | — | m.p. = 187 |
| 114 | 2-OCH₃ | 5-CyHex | 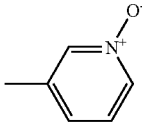 | H | 0 | 1 | 3 | — | m.p. = 113 |
| 115 | 2-OCH₃ | 5-CyHex | 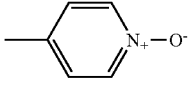 | H | 0 | 1 | 3 | — | m.p. = 242 |
| 116 | 2-OCH₃ | 5-CyHex |  | H | 0 | 1 | 3 | — | m.p. = 250 |

TABLE III-continued
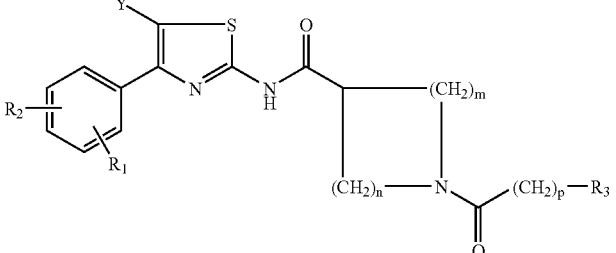
(I)
| N° | R₁ | R₂ | R₃ | Y | p | n | m | salt | m.p. and/or MH+, rt |
|---|---|---|---|---|---|---|---|---|---|
| 117 | 2-OCH₃ | 5-(CH₂)₃CH₃ | 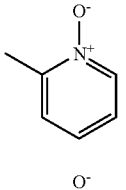 | H | 0 | 1 | 3 | — | m.p. = 134 |
| 118 | 2-OCH₃ | 5-CyPent | 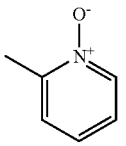 | H | 0 | 1 | 3 | — | m.p. = 160 |
| 119 | 2-OCH₂CH₃ | 5-(CH₂)₃CH₃ | 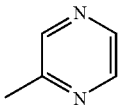 | H | 0 | 1 | 3 | — | m.p. = 152 |
| 120 | 2-OCH₃ | 5-CyHex | 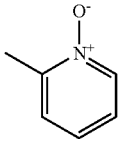 | H | 0 | 2 | 2 | — | m.p. = 129 |
| 121 (R) | 2-OCH₃ | 5-CyHex | 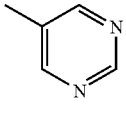 | H | 0 | 1 | 3 | — | m.p. = 178 |
| 122 | 2-OCH₃ | 5-CyHex | 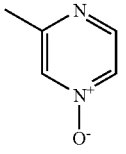 | H | 0 | 1 | 3 | — | m.p. = 138 |
| 123 | 2-OCH₃ | 5-CyHex | 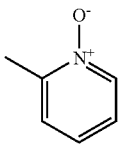 | H | 0 | 1 | 3 | — | m.p. = 143 |
| 124 (S) | 2-OCH₃ | 5-CyHex |  | H | 0 | 1 | 3 | — | m.p. = 181 |

TABLE III-continued
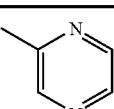
(I)
| N° | R₁ | R₂ | R₃ | Y | p | n | m | salt | m.p. and/or MH+, rt |
|---|---|---|---|---|---|---|---|---|---|
| 125 | 2-OCH₂CH₃ | 5-CyPent | 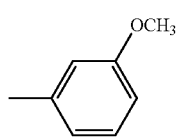 | H | 0 | 1 | 3 | — | m.p. = 206 |
| 126 | 2-OCH₃ | 5-O(CH₂)₂CH₃ | 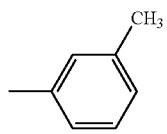 | H | 0 | 1 | 3 | — | MH+ = 510, rt = 10.16 |
| 127 | 2-OCH₃ | 5-O(CH₂)₂CH₃ | 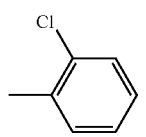 | H | 0 | 1 | 3 | — | MH+ = 494, rt = 10.45 |
| 128 | 2-OCH₃ | 5-O(CH₂)₂CH₃ | 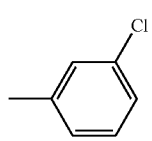 | H | 0 | 1 | 3 | — | MH+ = 514, rt = 10.41 |
| 129 | 2-OCH₃ | 5-O(CH₂)₂CH₃ | 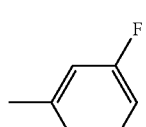 | H | 0 | 1 | 3 | — | MH+ = 514, rt = 10.57 |
| 130 | 2-OCH₃ | 5-O(CH₂)₂CH₃ | 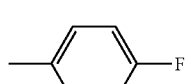 | H | 0 | 1 | 3 | — | MH+ = 498, rt = 10.22 |
| 131 | 2-OCH₃ | 5-O(CH₂)₂CH₃ | 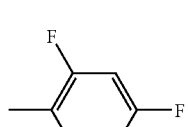 | H | 0 | 1 | 3 | — | MH+ = 498, rt = 10.18 |
| 132 | 2-OCH₃ | 5-O(CH₂)₂CH₃ | 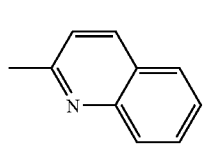 | H | 0 | 1 | 3 | — | MH+ = 516, rt = 10.31 |
| 133 | 2-OCH₃ | 5-O(CH₂)₂CH₃ |  | H | 0 | 1 | 3 | — | MH+ = 531, rt = 10.14 |

TABLE III-continued
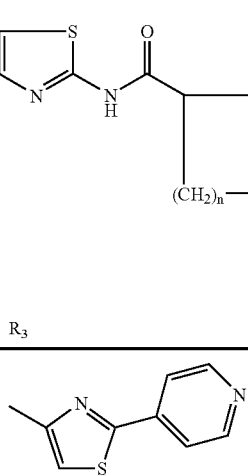
(I)
| N° | R₁ | R₂ | R₃ | Y | p | n | m | salt | m.p. and/or MH+, rt |
|---|---|---|---|---|---|---|---|---|---|
| 134 | 2-OCH₃ | 5-O(CH₂)₂CH₃ | 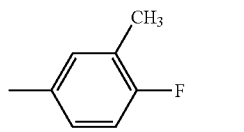 | H | 0 | 1 | 3 | — | MH+ = 564, rt = 8.66 |
| 135 | 2-OCH₃ | 5-O(CH₂)₂CH₃ |  | H | 0 | 1 | 3 | — | MH+ = 512, rt = 10.54 |
| 136 | 2-OCH₃ | 5-O(CH₂)₂CH₃ | 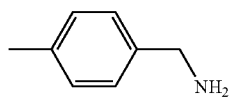 | H | 0 | 1 | 3 | — | MH+ = 486, rt = 10.07 |
| 137 | 2-OCH₃ | 5-O(CH₂)₂CH₃ | 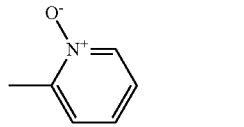 | H | 0 | 1 | 3 | — | MH+ = 509, rt = 6.83 |
| 138 | 2-OCH₃ | 5-O(CH₂)₂CH₃ | 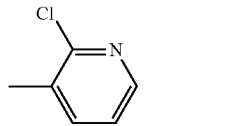 | H | 0 | 1 | 3 | — | MH+ = 497, rt = 8.33 |
| 139 | 2-OCH₃ | 5-O(CH₂)₂CH₃ | 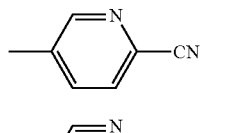 | H | 0 | 1 | 3 | — | MH+ = 515, rt = 9.58 |
| 140 | 2-OCH₃ | 5-O(CH₂)₂CH₃ | 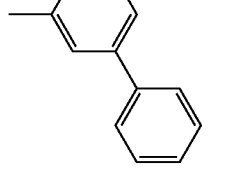 | H | 0 | 1 | 3 | — | MH+ = 506, rt = 9.59 |
| 141 | 2-OCH₃ | 5-O(CH₂)₂CH₃ | 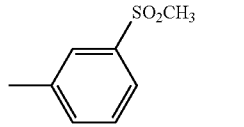 | H | 0 | 1 | 3 | — | MH+ = 557, rt = 10.03 |
| 142 | 2-OCH₃ | 5-O(CH₂)₂CH₃ |  | H | 0 | 1 | 3 | — | MH+ = 558, rt = 9.41 |

TABLE III-continued (I)

| N° | R₁ | R₂ | R₃ | Y | p | n | m | salt | m.p. and/or MH+, rt |
|---|---|---|---|---|---|---|---|---|---|
| 143 | 2-OCH₃ | 5-O(CH₂)₂CH₃ | 3,5-dimethyl-1-methylpyrazolyl | H | 0 | 1 | 3 | — | MH+ = 498, rt = 9.46 |
| 144 | 2-OCH₃ | 5-O(CH₂)₂CH₃ | 1-methyl-2-methylimidazolyl | H | 0 | 1 | 3 | — | MH+ = 484, rt = 8.49 |
| 145 | 2-OCH₃ | 5-O(CH₂)₂CH₃ | 2,5-dimethylfuranyl | H | 0 | 1 | 3 | — | MH+ = 498, rt = 10.35 |
| 146 | 2-OCH₃ | 5-O(CH₂)₂CH₃ | 2-methylpyridin-5-yl | H | 0 | 1 | 3 | — | MH+ = 495, rt = 8.38 |
| 147 | 2-OCH₃ | 5-O(CH₂)₂CH₃ | 2-methyl-4-methoxyquinolinyl | H | 0 | 1 | 3 | — | MH+ = 561, rt = 10.11 |
| 148 | 2-OCH₃ | 5-O(CH₂)₂CH₃ | 2,5-dimethylpyrazinyl | H | 0 | 1 | 3 | — | MH+ = 494, rt = 11.0 |
| 149 | 2-OCH₃ | 5-(CH₂)₃CH₃ | 2,4-dimethylthiazolyl | H | 0 | 1 | 3 | — | MH+ = 513, rt = 10.24 |
| 150 | 2-OCH₃ | 5-(CH₂)₃CH₃ | quinoxalinyl | H | 0 | 1 | 3 | — | MH+ = 530, rt = 10.04 |

TABLE III-continued
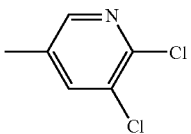
(I)
| N° | R₁ | R₂ | R₃ | Y | p | n | m | salt | m.p. and/or MH+, rt |
|---|---|---|---|---|---|---|---|---|---|
| 151 | 2-OCH₃ | 5-CyHex | 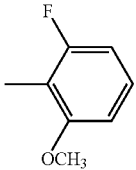 | H | 0 | 1 | 3 | — | MH+ = 573, rt = 11.67 |
| 152 | 2-OCH₃ | 5-CyHex | 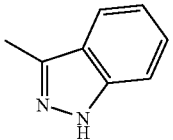 | H | 0 | 1 | 3 | — | MH+ = 552, rt = 11.39 |
| 153 | 2-OCH₃ | 5-CyHex | 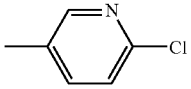 | H | 0 | 1 | 3 | — | MH+ = 544, rt = 11.02 |
| 154 | 2-OCH₃ | 5-O(CH₂)₂CH₃ | 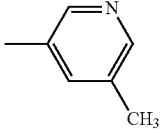 | H | 0 | 1 | 3 | — | MH+ = 515, rt = 9.80 |
| 155 | 2-OCH₃ | 5-O(CH₂)₂CH₃ | 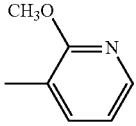 | H | 0 | 1 | 3 | — | MH+ = 495, rt = 8.74 |
| 156 | 2-OCH₃ | 5-O(CH₂)₂CH₃ | 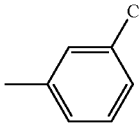 | H | 0 | 1 | 3 | — | MH+ = 511, rt = 9.64 |
| 157 | 2-OCH₃ | 5-O(CH₂)₂CH₃ | 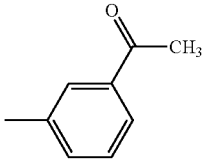 | H | 0 | 1 | 3 | — | MH+ = 505, rt = 9.89 |
| 158 | 2-OCH₃ | 5-O(CH₂)₂CH₃ |  | H | 0 | 1 | 3 | — | MH+ = 522, rt = 9.78 |

TABLE III-continued
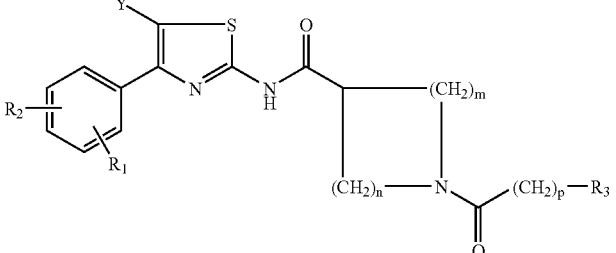
(I)
| N° | R₁ | R₂ | R₃ | Y | p | n | m | salt | m.p. and/or MH+, rt |
|---|---|---|---|---|---|---|---|---|---|
| 159 | 2-OCH₃ | 5-O(CH₂)₂CH₃ | 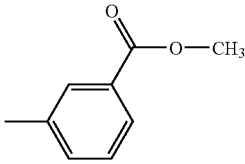 | H | 0 | 1 | 3 | — | MH+ = 538, rt = 10.10 |
| 160 | 2-OCH₃ | 5-(CH₂)₃CH₃ | 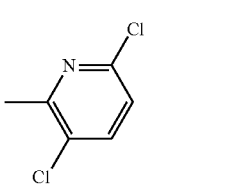 | H | 0 | 1 | 3 | — | MH+ = 560, rt = 11.25 |
| 161 | 2-OCH₃ | 5-(CH₂)₃CH₃ | 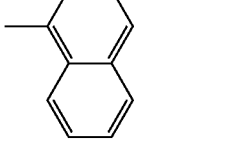 | H | 0 | 1 | 3 | — | MH+ = 547, rt = 11.07 |
| 162 | 2-OCH₃ | 5-(CH₂)₃CH₃ | 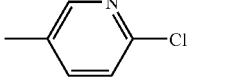 | H | 0 | 1 | 3 | — | MH+ = 529, rt = 10.69 |
| 163 | 2-OCH₃ | 5-(CH₂)₃CH₃ | 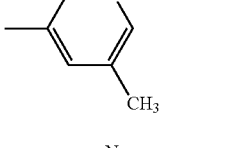 | H | 0 | 1 | 3 | — | MH+ = 513, rt = 10.62 |
| 164 | 2-OCH₃ | 5-(CH₂)₃CH₃ | 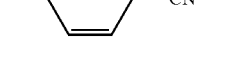 | H | 0 | 1 | 3 | — | MH+ = 493, rt = 6.52 |
| 165 | 2-OCH₃ | 5-(CH₂)₃CH₃ | 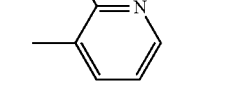 | H | 0 | 1 | 3 | — | MH+ = 504, rt = 10.38 |
| 166 | 2-OCH₃ | 5-(CH₂)₃CH₃ |  | H | 0 | 1 | 3 | — | MH+ = 509, rt = 10.46 |

TABLE III-continued
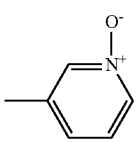
(I)
| N° | R₁ | R₂ | R₃ | Y | p | n | m | salt | m.p. and/or MH+, rt |
|---|---|---|---|---|---|---|---|---|---|
| 167 | 2-OCH₃ | 5-(CH₂)₃CH₃ | 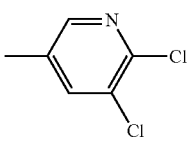 | H | 0 | 1 | 3 | — | MH+ = 495, rt = 8.96 |
| 168 | 2-OCH₃ | 5-(CH₂)₃CH₃ | 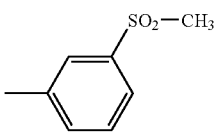 | H | 0 | 1 | 3 | — | MH+ = 547, rt = 11.24 |
| 169 | 2-OCH₃ | 5-(CH₂)₃CH₃ | 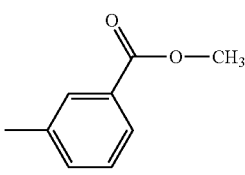 | H | 0 | 1 | 3 | — | MH+ = 556, rt = 10.19 |
| 170 | 2-OCH₃ | 5-(CH₂)₃CH₃ | 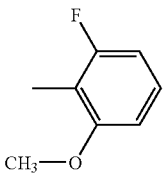 | H | 0 | 1 | 3 | — | MH+ = 536, rt = 10.84 |
| 171 | 2-OCH₃ | 5-(CH₂)₃CH₃ | 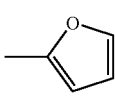 | H | 0 | 1 | 3 | — | MH+ = 526, rt = 10.98 |
| 172 | 2-OCH₃ | 5-(CH₂)₃CH₃ | 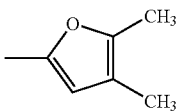 | H | 0 | 1 | 3 | — | MH+ = 468, rt = 10.56 |
| 173 | 2-OCH₃ | 5-(CH₂)₃CH₃ | 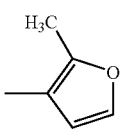 | H | 0 | 1 | 3 | — | MH+ = 496, rt = 11.17 |
| 174 | 2-OCH₃ | 5-(CH₂)₃CH₃ |  | H | 0 | 1 | 3 | — | MH+ = 482, rt = 10.77 |

TABLE III-continued
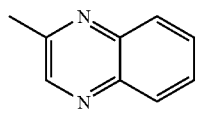
(I)
| N° | R₁ | R₂ | R₃ | Y | p | n | m | salt | m.p. and/or MH+, rt |
|---|---|---|---|---|---|---|---|---|---|
| 175 | 2-OCH₃ | 5-(CH₂)₃CH₃ | 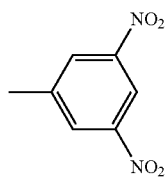 | H | 0 | 1 | 3 | — | MH+ = 530, rt = 10.79 |
| 176 | 2-OCH₃ | 5-(CH₂)₃CH₃ | 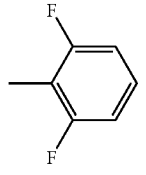 | H | 0 | 1 | 3 | — | MH+ = 568, rt = 14.07 |
| 177 | 2-OCH₃ | 5-(CH₂)₃CH₃ | 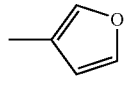 | H | 0 | 1 | 3 | — | MH+ = 514, rt = 11.07 |
| 178 | 2-OCH₃ | 5-(CH₂)₃CH₃ | 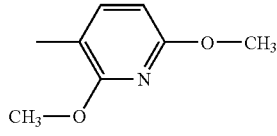 | H | 0 | 1 | 3 | — | MH+ = 468, rt = 10.45 |
| 179 | 2-OCH₃ | 5-(CH₂)₃CH₃ | 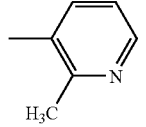 | H | 0 | 1 | 3 | — | MH+ = 539, rt = 11.11 |
| 180 | 2-OCH₃ | 5-(CH₂)₃CH₃ | 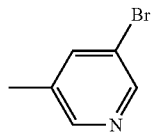 | H | 0 | 1 | 3 | — | MH+ = 493, rt = 8.91 |
| 181 | 2-OCH₃ | 5-(CH₂)₃CH₃ | 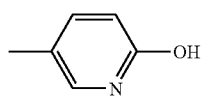 | H | 0 | 1 | 3 | — | MH+ = 558, rt = 10.62 |
| 182 | 2-OCH₃ | 5-(CH₂)₃CH₃ | 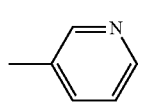 | H | 0 | 1 | 3 | — | MH+ = 495, rt = 9.04 |
| 183 | 2-OCH₃ | 5-(CH₂)₃CH₃ |  | H | 2 | 1 | 3 | — | MH+ = 507, rt = 7.84 |

TABLE III-continued
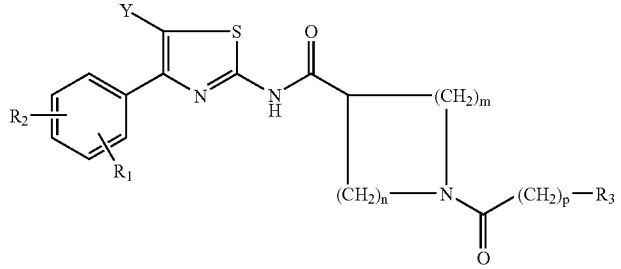
(I)
| N° | R₁ | R₂ | R₃ | Y | p | n | m | salt | m.p. and/or MH+, rt |
|---|---|---|---|---|---|---|---|---|---|
| 184 | 2-OCH₃ | 5-(CH₂)₃CH₃ | 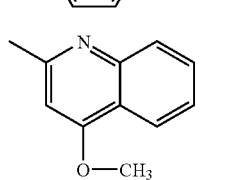 | H | 1 | 1 | 3 | — | MH+ = 493, rt = 8.01 |
| 185 | 2-OCH₃ | 5-(CH₂)₃CH₃ | 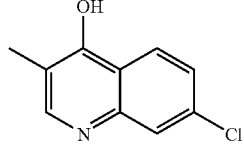 | H | 0 | 1 | 3 | — | MH+ = 559, rt = 10.88 |
| 186 | 2-OCH₃ | 5-(CH₂)₃CH₃ | 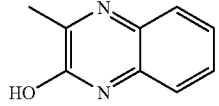 | H | 0 | 1 | 3 | — | MH+ = 579, rt = 9.99 |
| 187 | 2-OCH₃ | 5-(CH₂)₃CH₃ | 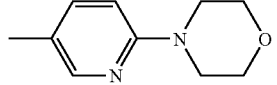 | H | 0 | 1 | 3 | — | MH+ = 546, rt = 9.93 |
| 188 | 2-OCH₃ | 5-(CH₂)₃CH₃ | 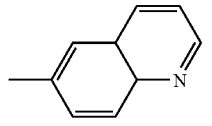 | H | 0 | 1 | 3 | — | MH+ = 564, rt = 9.78 |
| 189 | 2-OCH₃ | 5-(CH₂)₃CH₃ | 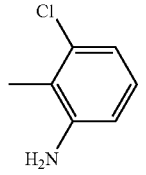 | H | 0 | 1 | 3 | — | MH+ = 529, rt = 9.57 |
| 190 | 2-OCH₃ | 5-CyHex | 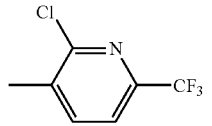 | H | 0 | 1 | 3 | — | MH+ = 553, rt = 11.38 |
| 191 | 2-OCH₃ | 5-CyHex | 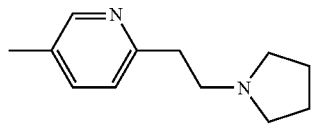 | H | 0 | 1 | 3 | — | MH+ = 607, rt = 11.80 |
| 192 | 2-OCH₃ | 5-CyHex |  | H | 0 | 1 | 3 | — | MH+ = 602, rt = 7.68 |

TABLE III-continued

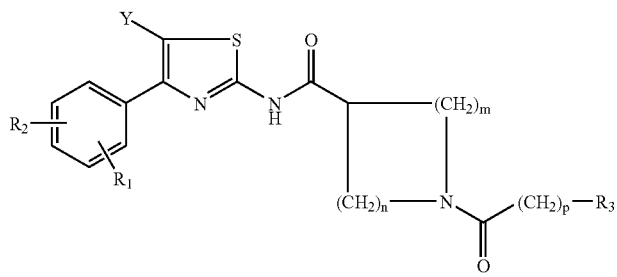

(I)

| N° | R₁ | R₂ | R₃ | Y | p | n | m | salt | m.p. and/or MH+, rt |
|---|---|---|---|---|---|---|---|---|---|
| 193 | 2-OCH₃ | 5-CyHex | 3-methyl-4-CF₃-pyridyl | H | 0 | 1 | 3 | — | MH+ = 573, rt = 11.09 |
| 194 | 2-OCH₃ | 5-CyHex | 3-methyl-5-methyl-2,6-dimethoxypyridyl | H | 0 | 1 | 3 | — | MH+ = 565, rt = 11.53 |
| 195 (S) | 2-OCH₃ | 5-CyHex | 5-methylpyridyl N-oxide | H | 0 | 1 | 3 | — | MH+ = 521 rt = 9.37 m.p. = 137 |
| 196 | 2-OCH₃ | 5-CyHex | 3-methyl-2,6-dichloro-5-fluoropyridyl | H | 0 | 1 | 3 | — | MH+ = 591, rt = 11.84 |
| 197 | 2-OCH₃ | 5-CyHex | 2-methyl-4-methoxyquinolinyl | H | 0 | 1 | 3 | — | MH+ = 584, rt = 11.33 |
| 198 | 2-OCH₃ | 5-CyHex | 6-methylquinolinyl | H | 0 | 1 | 3 | — | MH+ = 554, rt = 9.99 |
| 199 | 2-OCH₂CH₃ | 5-CH₂CH₃ | 5-methylpyrazinyl | H | 0 | 1 | 3 | — | MH+ = 466, rt = 9.42 |
| 200 | 2-OCH₂CH₃ | 5-CH₂CH₃ | 6-methyl-2-chloropyridyl | H | 0 | 1 | 3 | — | MH+ = 499, rt = 10.36 |

TABLE III-continued (I)

| N° | R₁ | R₂ | R₃ | Y | p | n | m | salt | m.p. and/or MH+, rt |
|---|---|---|---|---|---|---|---|---|---|
| 201 | 2-OCH₂CH₃ | 5-CH₂CH₃ | 3-cyanophenyl | H | 0 | 1 | 3 | — | MH+ = 489, rt = 10.23 |
| 202 | 2-OCH₂CH₃ | 5-CH₂CH₃ | 3-acetylphenyl | H | 0 | 1 | 3 | — | MH+ = 506, rt = 10.12 |
| 203 | 2-OCH₂CH₃ | 5-CH₂CH₃ | 3-nitrophenyl | H | 0 | 1 | 3 | — | MH+ = 509, rt = 10.45 |
| 204 | 2-OCH₂CH₃ | 5-CH₂CH₃ | 2,4,6-trifluorophenyl | H | 0 | 1 | 3 | — | MH+ = 518, rt = 10.81 |
| 205 | 2-OCH₂CH₃ | 5-CH₂CH₃ | 1,3,5-trimethylpyrazol-4-yl | H | 0 | 1 | 3 | — | MH+ = 482, rt = 9.82 |
| 206 | 2-OCH₂CH₃ | 5-CH₂CH₃ | 5-chloro-1,4-dimethylpyrazol-3-yl | H | 0 | 1 | 3 | — | MH+ = 502, rt = 9.76 |
| 207 | 2-OCH₂CH₃ | 5-CH₂CH₃ | furan-2-yl | H | 0 | 1 | 3 | — | MH+ = 454, rt = 10.11 |
| 208 | 2-OCH₂CH₃ | 5-CH₂CH₃ | 2,5-dimethylfuran-3-yl | H | 0 | 1 | 3 | — | MH+ = 482, rt = 9.82 |

TABLE III-continued
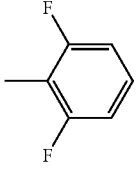
(I)
| N° | R₁ | R₂ | R₃ | Y | p | n | m | salt | m.p. and/or MH+, rt |
|---|---|---|---|---|---|---|---|---|---|
| 209 | 2-OCH₂CH₃ | 5-CH₂CH₃ | 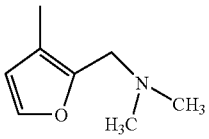 | H | 0 | 1 | 3 | — | MH+ = 500, rt = 10.66 |
| 210 | 2-OCH₂CH₃ | 5-CH₂CH₃ | 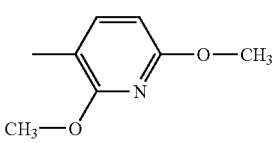 | H | 0 | 1 | 3 | — | MH+ = 511, rt = 7.16 |
| 211 | 2-OCH₂CH₃ | 5-CH₂CH₃ | 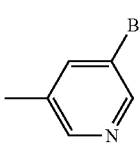 | H | 0 | 1 | 3 | — | MH+ = 525, rt = 10.60 |
| 212 | 2-OCH₂CH₃ | 5-CH₂CH₃ | 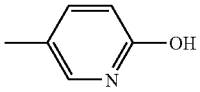 | H | 0 | 1 | 3 | — | MH+ = 543, rt = 10.17 |
| 213 | 2-OCH₂CH₃ | 5-CH₂CH₃ | 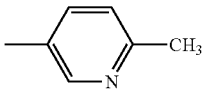 | H | 0 | 1 | 3 | — | MH+ = 481, rt = 8.61 |
| 214 | 2-OCH₂CH₃ | 5-CH₂CH₃ | 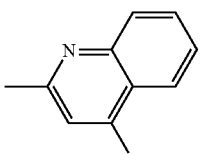 | H | 0 | 1 | 3 | — | MH+ = 479, rt = 8.69 |
| 215 | 2-OCH₂CH₃ | 5-CH₂CH₃ | 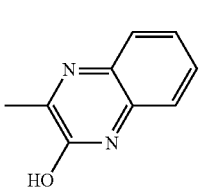 | H | 0 | 1 | 3 | — | MH+ = 545, rt = 10.45 |
| 216 | 2-OCH₂CH₃ | 5-CH₂CH₃ |  | H | 0 | 1 | 3 | — | MH+ = 532, rt = 9.51 |

TABLE III-continued
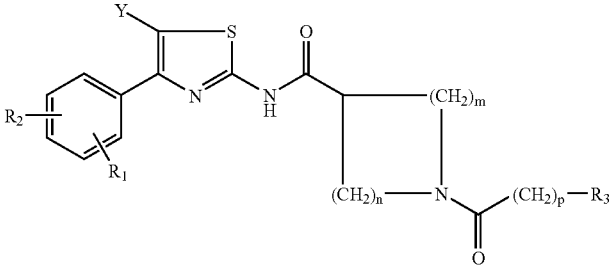
(I)
| N° | R₁ | R₂ | R₃ | Y | p | n | m | salt | m.p. and/or MH+, rt |
|---|---|---|---|---|---|---|---|---|---|
| 217 | 2-OCH₂CH₃ | 5-CH₂CH₃ | 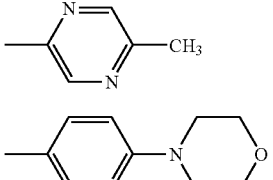 | H | 0 | 1 | 3 | — | MH+ = 480, rt = 9.62 |
| 218 | 2-OCH₂CH₃ | 5-CH₂CH₃ | 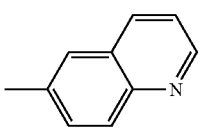 | H | 0 | 1 | 3 | — | MH+ = 550, rt = 9.35 |
| 219 | 2-OCH₂CH₃ | 5-CH₂CH₃ | 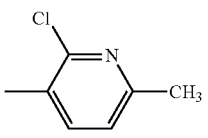 | H | 0 | 1 | 3 | — | MH+ = 515, rt = 9.13 |
| 220 | 2-OCH₃ | 5-(CH₂)₃CH₃ | 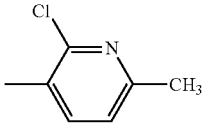 | H | 0 | 1 | 3 | — | MH+ = 527, rt = 10.62 |
| 221 | 2-OCH₃ | 5-CyHex | 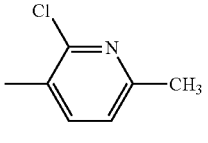 | H | 0 | 1 | 3 | — | MH+ = 553, rt = 11.10 |
| 222 | 2-OCH₃ | 5-O(CH₂)₂CH₃ | 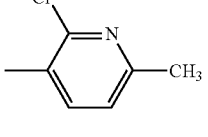 | H | 0 | 1 | 3 | — | MH+ = 529, rt = 9.82 |
| 223 | 2-OCH₂CH₃ | 5-CH₂CH₃ | 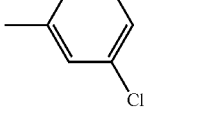 | H | 0 | 1 | 3 | — | MH+ = 513, rt = 10.17 |
| 224 | 2-OCH₃ | 5-O(CH₂)₂CH₃ | 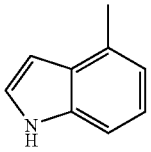 | H | 0 | 1 | 3 | — | MH+ = 515, rt = 9.96 |
| 225 | 2-OCH₃ | 5-(CH₂)₃CH₃ |  | H | 0 | 1 | 3 | — | MH+ = 517, rt = 10.55 |

TABLE III-continued

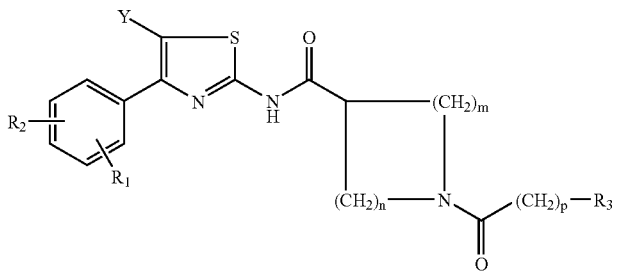

(I)

| N° | R₁ | R₂ | R₃ | Y | p | n | m | salt | m.p. and/or MH+, rt |
|---|---|---|---|---|---|---|---|---|---|
| 226 | 2-OCH₃ | 5-(CH₂)₃CH₃ | 2-methyl-4-chloropyridin-? | H | 0 | 1 | 3 | — | MH+ = 513, rt = 10.80 |
| 227 | 2-OCH₃ | 5-CyHex | 4-methyl-1H-indol-? | H | 0 | 1 | 3 | — | MH+ = 543, rt = 10.95 |
| 228 | 2-OCH₃ | 5-CyHex | 2-methyl-4-chloropyridin-? | H | 0 | 1 | 3 | — | MH+ = 539, rt = 11.31 |
| 229 | 2-OCH₃ | 5-CyHex | 2,6-dichloro-4-methylpyridin-? | H | 0 | 1 | 3 | — | MH+ = 573, rt = 11.72 |
| 230 | 2-OCH₂CH₃ | 5-CH₂CH₃ | 2-methyl-4-chloropyridin-? | H | 0 | 1 | 3 | — | MH+ = 499, rt = 10.33 |
| 231 | 2-OCH₃ | 5-(CH₂)₃CH₃ | 2-fluoro-3-methylpyridin-? | H | 0 | 1 | 3 | — | MH+ = 497, rt = 10.36 |
| 232 | 2-OCH₃ | 5-(CH₂)₃CH₃ | 1,2,5-trimethyl-pyrrol-? | H | 0 | 1 | 3 | — | MH+ = 509, rt = 10.95 |
| 233 | 2-OCH₃ | 5-CyHex | 1,2,5-trimethyl-pyrrol-? | H | 0 | 1 | 3 | — | MH+ = 535, rt = 11.38 |

TABLE III-continued (I)

| N° | R₁ | R₂ | R₃ | Y | p | n | m | salt | m.p. and/or MH+, rt |
|---|---|---|---|---|---|---|---|---|---|
| 234 | 2-OCH₂CH₃ | 5-CH₂CH₃ | (7-methylquinoxalinyl) | H | 0 | 1 | 3 | — | MH+ = 516, rt = 9.58 |
| 235 | 2-OCH₃ | 5-(CH₂)₂CH₃ | (3-methylpyridinyl) | H | 0 | 1 | 3 | HCl | m.p. = 172 |
| 236 | 2-OCH₃ | 5-(CH₂)₂CH₃ | (3-methylpyridinyl) | F | 0 | 1 | 3 | — | MH+ = 483, rt = 9.21, m.p. = 160 |
| 237 (S) | 2-OCH₃ | 5-CyHex | (1,3,5-trimethylpyrazolyl) | H | 0 | 1 | 3 | — | m.p. = 112 |
| 238 (S) | 2-OCH₃ | 5-CyHex | (4-methylpyrimidinyl) | H | 0 | 1 | 3 | — | m.p. = 124 |
| 239 (R) | 2-OCH₃ | 5-CyHex | (2-methylpyridinyl N-oxide) | H | 0 | 1 | 2 | — | m.p. = 155 |
| 240 (S) | 2-OCH₃ | 5-CyHex | (2-methylpyridinyl N-oxide) | H | 0 | 1 | 2 | — | m.p. = 157 |
| 241 | 2-OCH₃ | 5-CyHex | (2-methylpyridinyl N-oxide) | H | 0 | 1 | 3 | — | m.p. = 137 |
| 242 (S) | 2-OCH₂CH₃ | 5-CyPent | (2-methylpyridinyl N-oxide) | H | 0 | 1 | 3 | — | m.p. = 155 |

TABLE III-continued

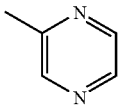
(I)

| N° | R₁ | R₂ | R₃ | Y | p | n | m | salt | m.p. and/or MH+, rt |
|---|---|---|---|---|---|---|---|---|---|
| 243 (S) | 2-OCH₂CH₃ | 5-CyPent | 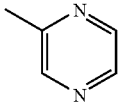 | H | 0 | 1 | 3 | — | m.p. = 137 |
| 244 (R) | 2-OCH₃ | 5-CyPent | 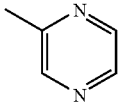 | H | 0 | 1 | 3 | — | m.p. = 117 |
| 245 (R) | 2-OCH₃ | 5-CyPent | 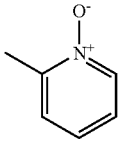 | H | 0 | 1 | 3 | — | m.p. = 160 |

The compounds according to the invention underwent pharmacological tests to determine their modulatory effect on the activity of the chemokine receptors.

Chemokines are low molecular weight proteins that belong to the family of proinflammatory cytokines and are involved in the chemotaxis of leukocytes and endothelial cells. Chemokines control many biological processes and are associated with inflammatory disorders appearing during states of stress, or during injury or infection; modulation of the effects of chemokines makes it possible to prevent or treat pathologies such as asthma, arthritis, allergies, autoimmune diseases, atherosclerosis or angiogenesis (C. D. Paavola et al., J. Biol. Chem., 1998, 273, (50), 33157-33165).

Among the chemokines, hMCP-1 (human monocyte chemotactic protein) is distinguished, which belongs to the group or CC chemokines and which is a natural agonist of the CCR2b receptor.

The inhibitory activity of the compounds according to the invention on cells expressing the human CCR2b receptor was measured. The concentration of natural hMCP-1 agonist that inhibits 50% (IC$_{50}$) of the activity of the CCR2b receptor is 0.57 nM. The compounds according to the invention have an IC$_{50}$ generally of less than 1 μM.

For example, compound 20 has an IC$_{50}$ of 25 nM, compound 31 has an IC$_{50}$ of 44 nM, compound 1 has an IC$_{50}$ of 290 nM and compound 107 has an IC$_{50}$ of 5 nM.

The inhibition of chemotaxis was also measured on human THP-1 monocytes (sold by DSMZ—Germany) using a technique adapted from that described by A. Albini et al., Cancer Res., 1987, 47, 3239-3245. Under these conditions, hMCP-1 has an IC$_{50}$ of 6 nM. The compounds according to the invention have an IC$_{50}$ generally of less than 1 μM.

The inhibition of chemotaxis by the compounds according to the invention is the sign of their antagonist activity on the chemokine receptors and in particular on CCR2b.

It thus appears that the compounds according to the invention are antagonists of the effect of chemokines, in particular of hMCP-1.

the compounds according to the invention may thus be used for the preparation of medicaments, in particular medicaments that antagonize the effect of chemokines.

Thus, according to another of its aspects, a subject of the present invention is medicaments that comprise a compound of formula (I), or an addition salt thereof with a pharmaceutically acceptable acid, or alternatively a hydrate or a solvate.

These medicaments find their use in therapy, especially in the prevention and treatment of various pathologies such as: acute and chronic autoimmune diseases and syndromes, for instance atherosclerosis, restinosis, chronic pulmonary diseases, in particular COPD (chronic obstructive pulmonary disease); respiratory distress syndrome; bronchial hyperactivity; colitis; silicosis; fibrous pathologies, pulmonary fibrosis, cystic fibrosis; viral or bacterial infections, AIDS (acquired immunodeficiency syndrome), meningitis, malaria, leprosy, tuberculosis, herpes, cytomegalovirus infections; septic shock, septicaemia, endotoxic shock; graft rejection; bone pathologies such as osteoporosis, osteoarthritis; conjunctivitis; atypic dermatitis or contact dermatitis; eczema; glomerulonephritis; pancreatitis; ulcerative colitis, autoimmune diseases, for instance rheumatoid arthritis, multiple sclerosis, amyotrophic lateral sclerosis, Crohn's disease, lupus erythematosis, scleroderma, psoriasis; Parkinson's disease; Alzheimer's disease; diabetes; cachexia; obesity;

treatment of cancer;

treatment of pain, in particular neuropathic and inflammatory pain;

allergic diseases, for instance allergic respiratory diseases, asthma, rhinitis, pulmonary hypersensitivity and delayed hypersensitivity;

diseases and disorders in which the angiogenic processes are involved )for example intratumoral angiogenesis), and retinal diseases (age-related macular degeneration: ARMD);

cardiac pathologies: haemodynamic shock; cardiac ischemias; post-ischemic reinfusion attack; myocardial infarction, coronary thrombosis, cardiac insufficiency, angina pectoris.

According to another of its aspects, the present invention relates to pharmaceutical compositions comprising, as active principle, a compound according to the invention. These pharmaceutically acceptable salt, a hydrate or solvate of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in unit administration form, as a mixture with standard pharmaceutical excipients, to man and animals for the prophylaxis or treatment of the above disorders or diseases.

the appropriate unit forms of administration include oral-route forms such as tablets, soft or hard gel capsules, powders, granules and oral solutions or suspensions, sublingual, buccal, intratracheal. intraocular or intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| | |
|---|---|
| Compound according to the invention | 50.0 mg |
| Mannitol | 223.75 mg |
| Croscaramellose sodium | 6.0 mg |
| Corn starch | 15.0 mg |
| Hydroxypropylmethylcellulose | 2.25 mg |
| Magnesium stearate | 3.0 mg |

Via the oral route, the dose of active principle administered per day may be from 0.1 to 1000 mg/kg, in one or more dosage intakes.

There may be particular cases in which higher or lower dosages are appropriate: such dosages do not depart from the context of the present invention. According to the usual practice, the dosage that is appropriate to each patient is determined by the doctor according to the mode of administration and the weight and response of the said patient.

According to another of its aspects, the present invention also relates to a method for treating the pathologies indicated above, which comprises the administration to a patient of an effective dose of a compound according to the invention, or a pharmaceutically acceptable salt or hydrate or solvate thereof.

What is claimed is:

1. A compound of formula (I):

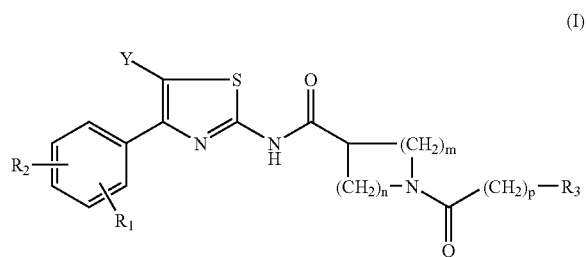

(I)

in which:
$R_1$ represents a hydrogen or halogen atom, a $(C_1-C_4)$alkyl, trifluoro$(C_1-C_4)$alkyl, hydroxyl, $(C_1-C_4)$alkoxy, trifluoro$(C_1-C_4)$alkoxy, $(C_3-C_{10})$cycloalkyl$(C_1-C_4)$alkoxy, $(C_3-C_{10})$cycloalkyloxy, allyloxy or $(C_1-C_4)$alkylthio group;

$R_2$ represents a hydrogen or halogen atom, a hydroxyl, $(C_1-C_4)$alkyl, trifluoro$(C_1-C_4)$alkyl, perfluoro$(C_1-C_4)$alkyl, $(C_3-C_{10})$cycloalkyl, $(C_1-C_4)$alkoxy, $(C_3-C_{10})$cycloalkyl$(C_1-C_4)$alkoxy, $(C_3-C_{10})$cycloalkyloxy, allyloxy or $(C_3-C_8)$cycloalkyl$(C_1-C_4)$alkyl group;

Y represents a hydrogen atom or a halogen;

$R_3$ represents:

a phenyl group substituted with one or more: fluorine, bromine, iodine, ethyl, propyl, isopropyl, butyl, isobutyl, tert-butyl, pentyl, $(C_1-C_6)$alkoxy,

—$NO_2$, cyano,

—$COR_4$,

—$SO_2R_4$,

—$CO_2R_4$, in which $R_4$ represents a $(C_1-C_4)$alkyl group, or

—$(CH_2)_q NR_5R_6$, in which $R_5$ and $R_6$ represent, independently of each other, a hydrogen atom or a $(C_1-C_4)$alkyl group or $R_5$ and $R_6$ form, together with the nitrogen atom to which they are attached, a 5- or 6-membered cycloalkyl group and q represents 0, 1 or 2;

or $R_3$ represents a heterocyclic group optionally substituted with one or more:

halogen, $(C_1-C_4)$alkyl, hydroxyl, $(C_1-C_4)$alkoxy, cyano, morpholine, trifluoro$(C_1-C_4)$alkyl,

—$COR_4$,

—$SO_2R_4$, in which $R_4$ is as defined hereinabove,

—$(CH_2)_q NR_5R_6$, in which $R_5$, $R_6$ and q are as defined hereinabove, phenyl, pyridine, or

—$SCH_3$;

the nitrogen atom(s) of the heterocyclic groups which comprise a nitrogen atom(s) may be optionally substituted with a $(C_1-C_4)$alkyl group, the nitrogen atom(s) of the heterocyclic groups which comprise a nitrogen atom(s) may be optionally in the N-oxide form;

or $R_3$ represents a heterobicyclic group optionally substituted with one or more halogen, hydroxyl, $(C_1-C_4)$alkyl or $(C_1-C_4)$alkoxy groups;

m represents 2, 3 or 4;

n represents 0, 1 or 2;

p represents 0, 1, 2 or 3;

or an addition salt of said compound with a pharmaceutically acceptable acid;

or a racemic mixture, enantiomer, diastereoisomer or mixture thereof of said compound or said salt.

2. A compound according to claim 1, of formula (I) in which:

$R_1$ and $R_2$ are as defined in claim 1;

Y represents a hydrogen atom or a halogen;

$R_3$ represents:

a phenyl group substituted with one or more: fluorine, bromine, iodine, ethyl, propyl, isopropyl, butyl, isobutyl, tert-butyl, pentryl, $(C_1-C_6)$alkoxy,

—$NO_2$, cyano,

—$COR_4$,

—$SO_2R_4$,

—$CO_2R_4$, in which $R_4$ represents a $(C_1-C_4)$alkyl group, or

—$(CH_2)_q NR_5R_6$, in which $R_5$, $R_6$ and q are as defined in claim 1;

or $R_3$ represents a heterocyclic group optionally substituted with one or more:

halogen, $(C_1-C_4)$alkyl, hydroxyl, $(C_1-C_4)$alkoxy, cyano, morpholine, trifluoro$(C_1-C_4)$alkyl,

—$COR_4$,

—$SO_2R_4$, in which $R_4$ is as defined in claim 1,

—$(CH_2)_q NR_5R_6$, in which $R_5$, $R_6$ and q are as defined in claim 1, phenyl, pyridine, or

—$SCH_3$;

the nitrogen atom(s) of the heterocyclic groups which comprise a nitrogen atom(s) may be optionally substituted with a $(C_1-C_4)$alkyl group, the nitrogen atom(s) of the heterocyclic groups which comprise a nitrogen atom(s) may be optionally in the N-oxide form;

or $R_3$ represents a heterobicyclic group optionally substituted with one or more halogen, hydroxyl, $(C_1-C_4)$alkyl or $(C_1-C_4)$alkoxy groups;

m represents 3;

n represents 1;

p represents 0;

or an addition salt of said compound with a pharmaceutically acceptable acid;

or a racemic mixture, enantiomer, diastereoisomer or mixture thereof of said compound or said salt.

3. A compound according to claim 1, of formula (I) in which:

$R_1$ and $R_2$ are as defined in claim 1;

Y is as defined in claim 1;

$R_3$ represents:

a phenyl group substituted with one or more:

fluorine bromine, iodine, ethyl, propyl, isopropyl, butyl, isobutyl, tert-butyl, pentryl, $(C_1-C_6)$alkoxy,

—$NO_2$, cyano,

—$COR_4$,

—$SO_2R_4$,

—$CO_2R_4$, in which $R_4$ represents a $(C_1-C_4)$alkyl group, or

—$(CH_2)_q NR_5R_6$, in which $R_5$, $R_6$ and q are as defined in claim 1;

or $R_3$ represents a heterocyclic group selected from pyridyl, pyrazinyl, pyrimidinyl, pyridazinyl, pyrazolyl, imidazolyl, thiazolyl, isothiazolyl, oxazolyl, isoxazolyl, oxadiazolyl, thiophenyl, pyrrolyl and furyl, the heterocyclic group being optionally substituted with one or more:

halogen, $(C_1-C_4)$alkyl, hydroxyl, $(C_1-C_4)$alkoxy, cyano, morpholine, trifluoro$(C_1-C_4)$alkyl,

—$COR_4$,

—$SO_2R_4$, in which $R_4$ is as defined in claim 1,

—$(CH_2)_q NR_5R_6$, in which $R_5$, $R_6$ and q are as defined in claim 1, phenyl, pyridine, or

—$SCH_3$;

the nitrogen atom(s) of the heterocyclic groups which comprise a nitrogen atom(s) may be optionally substituted with a $(C_1-C_4)$alkyl group, the nitrogen atom(s) of the heterocyclic groups which comprise a nitrogen atom(s) may be optionally in the N-oxide form;

or $R_3$ represents a heterobicyclic group selected from quinoxaline, quinoline, isoquinoline, indole, isoindole, indoline, indazole, benzothiazole, benzimidazole and benzoxazole, the heterobicyclic group being optionally substituted with one or more halogen, hydroxyl, $(C_1-C_4)$alkyl or $(C_1-C_4)$alkoxy groups;

m represents 3;

n represents 1;

p represents 0;

or an addition salt of said compound with a pharmaceutically acceptable acid;

or a racemic mixture, enantiomer, diastereoisomer or mixture thereof of said compound or said salt.

4. A compound according to claim 1, of formula (I) in which:

$R_1$ and $R_2$ are as defined in claim 1;

Y represents a hydrogen atom or a halogen;

$R_3$ represents:

a phenyl group substituted with one or more: fluorine, bromine, iodine, ethyl, propyl, isopropyl, butyl, isobutyl, tert-butyl, pentyl, $(C_1-C_6)$alkoxy,

—$NO_2$, cyano,

—$COR_4$,

—$SO_2R_4$,

—$CO_2R_4$, in which $R_4$ represents a $(C_1-C_4)$alkyl group, or

—$(CH_2)_q NR_5R_6$, in which $R_5$, $R_6$ and q are as defined in claim 1;

or $R_3$ represents a heterocyclic group optionally substituted with one or more:

halogen, $(C_1-C_4)$alkyl, hydroxyl,
($C_1$-$C_4$)alkoxy,
cyano,
morpholine,
trifluoro($C_1$-$C_4$)alkyl,
—$COR_4$,
—$SO_2R_4$, in which $R_4$ is as defined in claim 1,
—$(CH_2)_qNR_5R_6$, in which $R_5$, $R_6$ and q are as defined in claim 1,
phenyl,
pyridine, or
—$SCH_3$;
the nitrogen atom(s) of the heterocyclic groups which comprise a nitrogen atom(s) may be optionally substituted with a ($C_1$-$C_4$)alkyl group,
the nitrogen atom(s) of the heterocyclic groups which comprise a nitrogen atom(s) may be optionally in the N-oxide form;
or $R_3$ represents a heterobicyclic group optionally substituted with one or more halogen, hydroxyl, ($C_1$-$C_4$)alkyl or ($C_1$-$C_4$)alkoxy groups;
m represents 2 or 4;
n represents 0, 1 or 2;
p represents 0, 1, 2 or 3;
or an addition salt of said compound with a pharmaceutically acceptable acid;
or a racemic mixture, enantiomer, diastereoisomer or mixture thereof of said compound or said salt.

5. A compound according to claim 1, of formula (I) in which:
$R_1$ and $R_2$ are as defined in claim 1;
Y represents a hydrogen atom or a halogen;
$R_3$ represents:
a phenyl group substituted with one or more: fluorine, bromine, iodine,
ethyl, propyl, isopropyl, butyl, isobutyl, tert-butyl, pentyl,
($C_1$-$C_6$)alkoxy,
—$NO_2$,
cyano,
—$COR_4$,
—$SO_2R_4$,
—$CO_2R_4$, in which $R_4$ represents a ($C_1$-$C_4$)alkyl group,
—$(CH_2)_qNR_5R_6$, in which $R_5$, $R_6$ and q are as defined in claim 1;
or $R_3$ represents a heterocyclic group optionally substituted with one or more:
halogen,
($C_1$-$C_4$)alkyl,
hydroxyl,
($C_1$-$C_4$)alkoxy,
cyano,
morpholine,
trifluoro($C_1$-$C_4$)alkyl,
—$COR_4$,
—$SO_2R_4$, in which $R_4$ is as defined in claim 1,
—$(CH_2)_qNR_5R_6$, in which Rs, $R_6$ and q are as defined in claim 1,
phenyl,
pyridine, or
—$SCH_3$;
the nitrogen atom(s) of the heterocyclic groups which comprise a nitrogen atom(s) may be optionally substituted with a ($C_1$-$C_4$)alkyl group,
the nitrogen atom(s) of the heterocyclic groups which comprise a nitrogen atom(s) may be optionally in the N-oxide form;
or $R_3$ represents a heterobicyclic group optionally substituted with one or more halogen, hydroxyl, ($C_1$-$C_4$)alkyl or ($C_1$-$C_4$)alkoxy groups;
m represents 2, 3, or 4;
n represents 0, 1 or 2;
p represents 0, 1 or 2;
or an addition salt of said compound with a pharmaceutically acceptable acid;
or a racemic mixture, enantiomer, diastereoisomer or mixture thereof of said compound or said salt.

6. A compound according to claim 1, of formula (I) in which:
$R_1$ and $R_2$ are as defined in claim 1;
Y represents a hydrogen atom or a halogen;
$R_3$ represents:
a phenyl group substituted with one or more:
fluorine, bromine, iodine,
ethyl, propyl, isopropyl, butyl, isobutyl, tert-butyl, pentyl,
($C_1$-$C_6$)alkoxy,
—$NO_2$,
cyano,
—$COR_4$,
—$SO_2R_4$,
—$CO_2R_4$, in which $R_4$ represents a ($C_1$-$C_4$)alkyl group, or
—$(CH_2)_qNR_5R_6$, in which $R_5$, $R_6$ and q are as defined in claim 1;
or $R_3$ represents a heterocyclic group selected from pyridyl, pyrazinyl, pyrimidinyl, pyridazinyl, pyrazolyl, imidazolyl, thiazolyl, isothiazolyl, oxazolyl, isoxazolyl, oxadiazolyl, thiophenyl, pyrrolyl and furyl, the heterocyclic group being optionally substituted with one or more:
halogen,
($C_1$-$C_4$)alkyl,
hydroxyl,
($C_1$-$C_4$)alkoxy,
cyano,
morpholine,
trifluoro($C_1$-$C_4$)alkyl,
—$COR_4$,
—$SO_2R_4$, in which $R_4$ is as defined in claim 1,
—$(CH_2)_qNR_5R_6$, in which $R_5$, $R_6$ and q are as defined in claim 1,
phenyl,
pyridine, or
—$SCH_3$;
the nitrogen atom(s) of the heterocyclic groups which comprise a nitrogen atom(s) may be optionally substituted with a ($C_1$-$C_4$)alkyl group,
the nitrogen atom(s) of the heterocyclic groups which comprise a nitrogen atom(s) may be optionally in the N-oxide form;
or $R_3$ represents a heterobicyclic group selected from quinoxaline, quinoline, isoquinoline, indole, isoindole, indoline, indazole, benzothiazole, benzimidazole and benzoxazole, the heterobicyclic group being optionally substituted with one or more halogen, hydroxyl, ($C_1$-$C_4$) alkyl or ($C_1$-$C_4$)alkoxy groups;
m represents 2 or 4;
n represents 0, 1 or 2;
p represents 0, 1, 2 or 3;
or an addition salt of said compound with a pharmaceutically acceptable acid;
or a racemic mixture, enantiomer, diastereoisomer or mixture thereof of said compound or said salt.

7. A compound according to claim 1, of formula (I) in which:

$R_1$ and $R_2$ are as defined in claim 1;
Y represents a hydrogen atom or a halogen;
$R_3$ represents:
a phenyl group substituted with one or more:
fluorine, bromine, iodine,
ethyl, propyl, isopropyl, butyl, isobutyl, tert-butyl, pentyl, $(C_1-C_6)$alkoxy,
—$NO_2$,
cyano,
—$COR_4$,
—$SO_2R_4$,
—$CO_2R_4$, in which $R_4$ represents a $(C_1-C_4)$alkyl group, or
—$(CH_2)_qNR_5R_6$, in which $R_5$, $R_6$ and q are as defined in claim 1;
or $R_3$ represents a heterocyclic group selected from pyridyl, pyrazinyl, pyrimidinyl, pyridazinyl, pyrazolyl, imidazolyl, thiazolyl, isothiazolyl, oxazolyl, isoxazolyl, oxadiazolyl, thiophenyl, pyrrolyl and furyl, the heterocyclic group being optionally substituted with one or more:
halogen,
$(C_1-C_4)$alkyl,
hydroxyl,
$(C_1-C_4)$alkoxy,
cyano,
morpholine,
trifluoro$(C_1-C_4)$alkyl,
—$COR_4$,
—$SO_2R_4$, in which $R_4$ is as defined in claim 1,
—$(CH_2)_qNR_5R_6$, in which $R_5$, $R_6$ and q are as defined in claim 1,
phenyl,
pyridine, or
—$SCH_3$;
the nitrogen atom(s) of the heterocyclic groups which comprise a nitrogen atom(s) may be optionally substituted with a $(C_1-C_4)$alkyl group,
the nitrogen atom(s) of the heterocyclic groups which comprise a nitrogen atom(s) may be optionally in the N-oxide form;
or $R_3$ represents a heterobicyclic group selected from quinoxaline, quinoline, isoquinoline, indole, isoindole, indoline, indazole, benzothiazole, benzimidazole and benzoxazole, the heterobicyclic group being optionally substituted with one or more halogen, hydroxyl, $(C_1-C_4)$ alkyl or $(C_1-C_4)$alkoxy groups;
m represents 2, 3 or 4;
n represents 0, 1 or 2;
p represents 0, 1 or 2;
or an addition salt of said compound with a pharmaceutically acceptable acid;
or a racemic mixture, enantiomer, diastereoisomer or mixture thereof of said compound or said salt.

8. A compound according to claim 1, of formula (I) in which:

$R_1$ and $R_2$ are as defined in claim 1;
Y represents a hydrogen atom or a halogen;
$R_3$ represents:
a phenyl group substituted with one or more:
fluorine, bromine, iodine,
ethyl, propyl, isopropyl, butyl, isobutyl, tert-butyl, pentyl, $(C_1-C_6)$alkoxy,
—$NO_2$,
cyano,
—$COR_4$,
—$SO_2R_4$,
—$CO_2R_4$, in which $R_4$ represents a $(C_1-C_4)$alkyl group, or
—$(CH_2)_qNR_5R_6$, in which $R_5$, $R_6$ and q are as defined in claim 1;
or $R_3$ represents a heterocyclic group selected from pyridyl, pyrazinyl, pyrimidinyl, pyridazinyl, pyrazolyl, imidazolyl, thiazolyl, isothiazolyl, oxazolyl, isoxazolyl, oxadiazolyl, thiophenyl, pyrrolyl and furyl, the heterocyclic group being optionally substituted with one or more:
halogen,
$(C_1-C_4)$alkyl,
hydroxyl,
$(C_1-C_4)$alkoxy,
cyano,
morpholine,
trifluoro$(C_1-C_4)$alkyl,
—$COR_4$,
—$SO_2R_4$, in which $R_4$ is as defined in claim 1,
—$(CH_2)_qNR_5R_6$, in which $R_5$, $R_6$ and q are as defined in claim 1,
phenyl,
pyridine, or
—$SCH_3$;
the nitrogen atom(s) of the heterocyclic groups which comprise a nitrogen atom(s) may be optionally substituted with a $(C_1-C_4)$alkyl group,
the nitrogen atom(s) of the heterocyclic groups which comprise a nitrogen atom(s) may be optionally in the N-oxide form;
or $R_3$ represents a heterobicyclic group selected from quinoxaline, quinoline, isoquinoline, indole, isoindole, indoline, indazole, benzothiazole, benzimidazole and benzoxazole, the heterobicyclic group being optionally substituted with one or more halogen, hydroxyl, $(C_1-C_4)$ alkyl or $(C_1-C_4)$alkoxy groups;
m represents 2 or 4;
n represents 0, 1 or 2;
p represents 0, 1 or 2;
or an addition salt of said compound with a pharmaceutically acceptable acid;
or a racemic mixture, enantiomer, diastereoisomer or mixture thereof of said compound or said salt.

9. A compound according to claim 1, of formula (I) in which:

$R_1$ and $R_2$ are as defined in claim 1;
Y represents a hydrogen atom or a halogen;
$R_3$ represents:
a phenyl group substituted with one or more:
fluorine, bromine, iodine,
ethyl, propyl, isopropyl, butyl, isobutyl, tert-butyl, pentyl, $(C_1-C_6)$alkoxy,
—$NO_2$,
cyano,
—$COR_4$,
—$SO_2R_4$,
—$CO_2R_4$, in which $R_4$ represents a $(C_1-C_4)$alkyl group, or
—$(CH_2)_qNR_5R_6$, in which $R_5$, $R_6$ and q are as defined in claim 1;
or $R_3$ represents a heterocyclic group selected from pyridyl, pyrazinyl, pyrimidinyl, pyridazinyl, pyrazolyl, imidazolyl, thiazolyl, isothiazolyl, oxazolyl, isoxazolyl, oxadiazolyl, thiophenyl, pyrrolyl and furyl, the heterocyclic group being optionally substituted with one or more:
halogen,
$(C_1-C_4)$alkyl, hydroxyl,
($C_1$-$C_4$)alkoxy,
cyano,
morpholine,
trifluoro($C_1$-$C_4$)alkyl,
—$COR_4$,
—$SO_2R_4$, in which $R_4$ is as defined in claim 1,
—$(CH_2)_qNR_5R_6$, in which $R_5$, $R_6$ and q are as defined in claim 1,
phenyl,
pyridine, or
—$SCH_3$;
the nitrogen atom(s) of the heterocyclic groups which comprise a nitrogen atom(s) may be optionally substituted with a ($C_1$-$C_4$)alkyl group,
the nitrogen atom(s) of the heterocyclic groups which comprise a nitrogen atom(s) may be optionally in the N-oxide form;
or $R_3$ represents a heterobicyclic group selected from quinoxaline, quinoline, isoquinoline, indole, isoindole, indoline, indazole, benzothiazole, benzimidazole and benzoxazole, the heterobicyclic group being optionally substituted with one or more halogen, hydroxyl, ($C_1$-$C_4$) alkyl or ($C_1$-$C_4$)alkoxy groups;
m represents 2 or 4;
n represents 0, 1 or 2;
p represents 0;
or an addition salt of said compound with a pharmaceutically acceptable acid;
or a racemic mixture, enantiomer, diastereoisomer or mixture thereof of said compound or said salt.

10. A compound according to claim 1, selected from the group consisting of:
1-(1,5-dimethyl-1H-pyrazole-3-carbonyl)piperidine-3-carboxylic acid [4-(5-cyclohexyl-2-methoxyphenyl) thiazol-2-yl]amide;
1-(1-methyl-1H-imidazole-2-carbonyl)piperidine-3-carboxylic acid [4-(5-cyclohexyl-2-methoxyphenyl)thiazol-2-yl]amide;
1-(pyrimidine-4-carbonyl)piperidine-3-carboxylic acid [4-(5-cyclohexyl-2-methoxyphenyl)thiazol-2-yl] amide;
1-(pyrazine-2-carbonyl)piperidine-3-carboxylic acid [4-(5-cyclohexyl-2-ethoxyphenyl)thiazol-2-yl]amide;
1-(1-oxypyridine-2-carbonyl)piperidine-3-carboxylic acid [4-(5-cyclopentyl-2-methoxyphenyl)thiazol-2-yl] amide;
1-(2-hydroxypyridine-3-carbonyl)piperidine-3-carboxylic acid [4-(5-cyclohexyl-2-methoxyphenyl)thiazol-2-yl]amide;
1-(1-oxypyridine-3-carbonyl)piperidine-3-carboxylic acid [4-(5-cyclohexyl-2-methoxyphenyl)thiazol-2-yl] amide;
1-(5-chloro-1-methyl-1H-pyrazole-4-carbonyl)piperidine-3-carboxylic acid [4-(5-cyclohexyl-2-methoxyphenyl)thiazol-2-yl]amide;
1-(furan-2-carbonyl)piperidine-3-carboxylic acid [4-(5-cyclohexyl-2-methoxyphenyl)thiazol-2-yl]amide;
1-(pyrazine-2-carbonyl)piperidine-4-carboxylic acid [4-(5-cyclohexyl-2-methoxyphenyl)thiazol-2-yl]amide;
1-(pyrazine-2-carbonyl)piperidine-2-carboxylic acid [4-(5-cyclohexyl-2-methoxyphenyl)thiazol-2-yl]amide;
1-(2-pyridin-2-ylacetyl)piperidine-3-carboxylic acid [4-(5-cyclohexyl-2-methoxyphenyl)thiazol-2-yl]amide;
1-(1-oxypyridine-2-carbonyl)piperidine-3-carboxylic acid [4-(5-cyclohexyl-2-methoxyphenyl)thiazol-2-yl] amide;
(S)-1-(1-oxypyridine-2-carbonyl)piperidine-3-carboxylic acid [4-(5-cyclohexyl-2-methoxyphenyl)thiazol-2-yl] amide;
1-(pyrazine-2-carbonyl)piperidine-3-carboxylic acid [4-(5-cyclohexyl-2-methoxyphenyl)thiazol-2-yl]amide;
(S)-1-(pyrazine-2-carbonyl)piperidine-3-carboxylic acid [4-(5-cyclohexyl-2-methoxyphenyl)thiazol-2-yl] amide;
1-(1-oxypyridine-2-carbonyl)piperidine-3-carboxylic acid [4-(5-butyl-2-methoxyphenyl)thiazol-2-yl]amide;
1-(pyrazine-2-carbonyl)piperidine-3-carboxylic acid [4-(5-cyclopentyl-2-methoxyphenyl)thiazol-2-yl]amide;
(R)-1-(pyrazine-2-carbonyl)piperidine-3-carboxylic acid [4-(5-cyclohexyl-2-methoxyphenyl)thiazol-2-yl] amide;
1-(1-oxypyridine-2-carbonyl)pyrrolidine-3-carboxylic acid [4-(5-cyclohexyl-2-methoxyphenyl)thiazol-2-yl] amide; and
(R)-1-(1-oxypyridine-2-carbonyl)pyrrolidine-3-carboxylic acid [4-(5-cyclohexyl-2-methoxyphenyl)thiazol-2-yl]amide;

or an addition salt of said compound with a pharmaceutically acceptable acid.

11. A pharmaceutical composition comprising a compound of formula (I) according to claim 1, and at least one pharmaceutically acceptable excipient.

12. A pharmaceutical composition comprising a compound of formula (I) according to claim 2, and at least one pharmaceutically acceptable excipient.

13. A pharmaceutical composition comprising a compound of according to claim 10, and at least one pharmaceutically acceptable excipient.

14. A compound of formula (I):

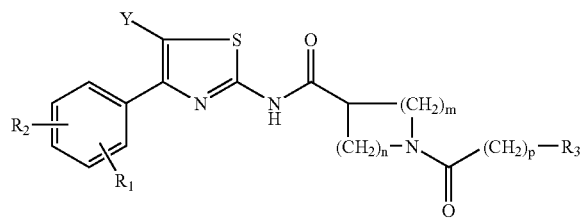

(I)

in which:
$R_1$ represents a hydrogen, chlorine, bromine, iodine, ethyl, propyl, Isopropyl, butyl, isobutyl, tert-butyl, trifluoro ($C_1$-$C_4$)alkyl, hydroxyl, -O-ethyl, -O-propyl, -O-isopropyl. -O-butyl, -O-isobutyl, -O-tert-butyl, trifluoro($C_1$-$C_4$)alkoxy, ($C_3$-$C_{10}$)cycloalkyl($C_1$-$C_4$)alkoxy, ($C_3$-$C_{10}$) cycloalkyloxy, allyloxy or ($C_1$-$C_4$)alkylthio group;
$R_2$ represents a hydrogen, chlorine, bromine, iodine, a hydroxyl, ($C_1$-$C_4$)alkyl, trifluoro($C_1$-$C_4$)alkyl, perfluoro ($C_1$-$C_4$)alkyl, ($C_3$-$C_{10}$)cycloalkyl, -O-ethyl, -O-propyl, -O-isopropyl, -O-butyl, -O-isobutyl, -O-tert-butyl, ($C_3$-$C_{10}$)cycloalkyl($C_1$-$C_4$)alkoxy, ($C_3$-$C_{10}$)cycloalkyloxy, allyloxy or ($C_3$-$C_{10}$)cycloalkyl($C_1$-$C_4$)alkyl group;
Y represents a hydrogen atom or a halogen;
$R_3$ represents:
a phenyl group substituted with one or more: halogen, ($C_1$-$C_6$)alkyl,
($C_1$-$C_6$)alkoxy,
—$NO_2$,
cyano,
—$COR_4$,

—SO$_2$R$_4$,

—CO$_2$R$_4$, in which R$_4$ represents a (C$_1$-C$_4$)alkyl group, or

—CH$_2$)$_q$NR$_5$R$_6$, in which R$_5$ and R$_6$ represent, independently of each other, a hydrogen atom or a (C$_1$-C$_4$)alkyl group or R5 and R6 form, together with the nitrogen atom to which they are attached, a 5- or 6-membered cycloalkyl group and q represents 0, 1 or 2;

or R$_3$ represents a heterocyclic group optionally substituted with one or more:

halogen, (C$_1$-C$_4$)alkyl, hydroxyl, (C$_1$-C$_4$)alkoxy, cyano, morpholine, trifluoro(C$_1$-C$_4$)alkyl,

—COR$_4$,

—SO$_2$R$_4$, in which R$_4$ is as defined hereinabove,

—(CH$_2$)$_q$NR$_5$R$_6$, in which R$_5$, R$_6$ and q are as defined hereinabove, phenyl, pyridine, or

—SCH$_3$;

the nitrogen atom(s) of the heterocyclic groups which comprise a nitrogen atom(s) may be optionally substituted with a (C$_1$-C$_4$)alkyl group, the nitrogen atom(s) of the heterocyclic groups which comprise a nitrogen atom(s) may be optionally in the N-oxide form;

or R$_3$ represents a heterobicyclic group optionally substituted with one or more halogen, hydroxyl, (C$_1$-C$_4$)alkyl or (C$_1$-C$_4$)alkoxy groups;

m represents 2, 3 or 4;

n represents 0, 1 or 2;

p represents 0, 1, 2 or 3;

or an addition salt of said compound with a pharmaceutically acceptable acid;

or a racemic mixture, enantiomer, diastereoisomer or mixture thereof of said compound or said salt.

15. A pharmaceutical composition comprising a compound of formula (I) according to claim 14, and at least one pharmaceutically acceptable excipient.

16. A compound of formula (I):

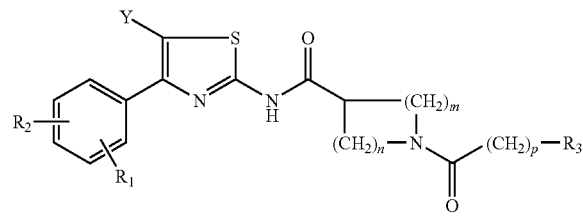

(I)

in which:

R$_1$ represents a hydrogen or halogen atom, a (C$_1$-C$_4$)alkyl, trifluoro(C$_1$-C$_4$)alkyl, hydroxyl, (C$_1$-C$_4$)alkoxy, trifluoro(C$_1$-C$_4$)alkoxy, (C$_3$-C$_{10}$)cycloalkyl(C$_1$-C$_4$)alkoxy, (C$_3$-C$_{10}$)cycloalkyloxy, allyloxy or (C$_1$-C$_4$)alkylthio group;

R$_2$ represents a hydrogen or halogen atom, a hydroxyl, (C$_1$-C$_4$)alkyl, trifluoro(C$_1$-C$_4$)alkyl, perfluoro(C$_1$-C$_4$alkyl, (C$_3$-C$_{10}$)cycloalkyl, (C$_1$-C$_4$alkoxy, (C$_3$-C$_{10}$)cycloalkyl(C$_1$-C$_4$)alkoxy, (C$_3$-C$_{10}$)cycloalkyloxy, allyloxy or (C$_3$-C$_8$)cycloalkyl(C$_1$-C$_4$)alkyl group;

Y represents a hydrogen atom or a halogen;

R$_3$ represents:

a phenyl group substituted with one or more: fluorine, bromine, iodine, (C$_1$-C$_6$)alkyl, (C$_1$-C$_6$)alkoxy,

—NO$_2$, cyano,

—COR$_4$,

SO$_2$R$_4$,

—C$_2$R$_1$, in which R$_4$ represents a (C$_1$-C$_4$)alkyl group, or

—(CH$_2$)$_q$NR$_5$R$_6$, in which R$_5$ and R$_6$ represent, independently of each other, a hydrogen atom or a (C$_1$-C$_4$)alkyl group or R$_5$ and R$_6$ form, together with the nitrogen atom to which they are attached, a 5- or 6-membered cycloalkyl group and q represents 0, 1 or 2;

or R$_3$ represents a heterocyclic group optionally substituted with one or more:

halogen, (C$_1$-C$_4$)alkyl, hydroxyl, (C$_1$-C$_4$)alkoxy, cyano, morpholine, trifluoro(C$_1$-C$_4$)alkyl,

—COR$_4$,

—SO$_2$R$_4$, in which R$_4$ is as defined hereinabove,

—(CH$_2$)$_q$NR$_5$R$_6$, in which R$_5$, R$_6$ and q are as defined hereinabove, phenyl, pyridine, or

—SCH$_3$;

the nitrogen atom(s) of the heterocyclic groups which comprise a nitrogen atom(s) may be optionally substituted with a (C$_1$-C$_4$)alkyl group, the nitrogen atom(s) of the heterocyclic groups which comprise a nitrogen atom(s) may be optionally in the N-oxide form;

or R$_3$ represents a heterobicyclic group optionally substituted with one or more halogen, hydroxyl, (C$_1$-C$_4$)alkyl or (C$_1$-C$_4$)alkoxy groups;

m represents 3 or 4;

n represents 0, 1 or 2;

p represents 0, 1,2 or 3;

or an addition salt of said compound with a pharmaceutically acceptable acid;

or a racemic mixture, enantiomer, diastereoisomer or mixture thereof of said compound or said salt.

17. A pharmaceutical composition comprising a compound of formula (I) according to claim 16, and at least one pharmaceutically acceptable excipient.

* * * * *

UNITED STATES PATENT AND TRADEMARK OFFICE
CERTIFICATE OF CORRECTION

PATENT NO.        : 7,598,392 B2                                                        Page 1 of 2
APPLICATION NO.   : 11/736770
DATED             : October 6, 2009
INVENTOR(S)       : Pierre Casellas et al.

It is certified that error appears in the above-identified patent and that said Letters Patent is hereby corrected as shown below:

In column 27, line 46, delete "ioxane" and insert -- dioxane --, therefor.

In column 28, line 41, delete "organ ic" and insert -- organic --, therefor.

In column 53, Table III, under 101, delete "  " and insert --  --, therefor.

In column 85, Table III, under 241, delete "  " and insert --  --, therefor.

In column 87, line 53, delete "or" and insert -- of --, therefor.

In column 88, line 55, delete "restinosis," and insert -- restenosis, --, therefor.

In column 89, line 1, delete "erythematosis," and insert -- erythematosus, --, therefor.

In column 89, line 19, after "These" insert -- pharmaceutical compositions contain an effective dose of at least one compound according to the invention, or a --.

In column 89, line 38, delete "intratracheal." and insert -- intratracheal, --, therefor.

In column 91, line 18, in Claim 2, delete "pentryl," and insert -- pentyl, --, therefor.

In column 91, line 66, in Claim 3, delete "fluorine" and insert -- fluorine, --, therefor.

In column 93, line 42, in Claim 5, after "group," insert -- or --.

In column 93, line 57, in Claim 5, delete "Rs," and insert -- $R_5$, --, therefor.

In column 97, line 32, in Claim 10, after "compound" delete "according to claim 1,".

Signed and Sealed this

Sixteenth Day of November, 2010

David J. Kappos
*Director of the United States Patent and Trademark Office*

CERTIFICATE OF CORRECTION (continued)
U.S. Pat. No. 7,598,392 B2

In column 98, line 51, in Claim 14, delete "-O-isopropyl." and insert -- -O-isopropyl, --, therefor.

In column 98, line 59, in Claim 14, delete "($C_3$-$C_{10}$)" and insert -- ($C_3$-$C_8$) --, therefor.

In column 99, line 5, in Claim 14, delete "R5 and R6" and insert -- $R_5$ and $R_6$ --, therefor.

In column 100, line 2-3, in Claim 16, delete "($C_1$-$C_4$alkyl," and insert -- ($C_1$-$C_4$)alkyl, --, therefor.

In column 100, line 3, in Claim 16, delete "($C_1$-$C_4$alkoxy," and insert -- ($C_1$-$C_4$)alkoxy, --, therefor.

In column 100, line 16, in Claim 16, delete "$SO_2R_4$," and insert -- —$SO_2R_4$, --, therefor.

In column 100, line 17, in Claim 16, delete "—$C_2R_1$," and insert -- —$CO_2R_4$, --, therefor.